(12) United States Patent
Vaughan et al.

(10) Patent No.: US 12,402,840 B2
(45) Date of Patent: Sep. 2, 2025

(54) METHODS AND APPARATUS TO DETERMINE DEVELOPMENTAL PROGRESS WITH ARTIFICIAL INTELLIGENCE AND USER INPUT

(71) Applicant: Cognoa, Inc., Palo Alto, CA (US)

(72) Inventors: Brent Vaughan, Portola Valley, CA (US); Clara Lajonchere, Los Angeles, CA (US); Dennis Wall, Palo Alto, CA (US); Jay Hack, Ann Arbor, MI (US); Charlie Hack, New York, NY (US)

(73) Assignee: Cognoa, Inc., Palo Alto, CA (US)

( * ) Notice: Subject to any disclaimer, the term of this patent is extended or adjusted under 35 U.S.C. 154(b) by 507 days.

(21) Appl. No.: 16/951,915

(22) Filed: Nov. 18, 2020

(65) Prior Publication Data
US 2021/0068766 A1   Mar. 11, 2021

Related U.S. Application Data

(63) Continuation of application No. 15/234,814, filed on Aug. 11, 2016, now Pat. No. 10,874,355.
(Continued)

(51) Int. Cl.
*A61B 5/00* (2006.01)
*A61B 5/16* (2006.01)
(Continued)

(52) U.S. Cl.
CPC .............. *A61B 5/7275* (2013.01); *A61B 5/00* (2013.01); *A61B 5/16* (2013.01); *G16H 10/20* (2018.01);
(Continued)

(58) Field of Classification Search
CPC .......... A61B 5/7275; A61B 5/00; A61B 5/16; A61B 5/168; A61B 1/00–2576/026;
(Continued)

(56) References Cited

U.S. PATENT DOCUMENTS

| 4,860,214 A | 8/1989 | Matsuda et al. |
| 5,722,418 A | 3/1998 | Bro |

(Continued)

FOREIGN PATENT DOCUMENTS

| CA | 2857069 A1 | 5/2013 |
| CN | 1918575 A | 2/2007 |

(Continued)

OTHER PUBLICATIONS

Kosmicki et al., "Searching for a minimal set of behaviors for autism detection through feature selection-based machine learning," Transl Psychiatry (2015) 5, e514; doi:10-1038/tp.2015.7 (Year: 2015).*

(Continued)

*Primary Examiner* — Jonathon A. Szumny
(74) *Attorney, Agent, or Firm* — Wilson Sonsini Goodrich & Rosati

(57) ABSTRACT

The methods and apparatus disclosed herein can diagnose or identify a subject as at risk of having one or more developmental disorders with fewer questions, decreased amounts of time, and determine a plurality of developmental disorders, and provide clinically acceptable sensitivity and specificity in a clinical environment. The methods and apparatus disclosed herein can be configured to diagnose or determine the subject as at risk of a developmental disorder among a plurality of developmental disorders, and decreasing the number of questions presented can be particularly helpful where a subject presents with a plurality of possible developmental disorders. A processor can be configured with instructions to identify a most predictive next question, such that a person can be diagnosed or identified as at risk with fewer questions.

37 Claims, 10 Drawing Sheets

Related U.S. Application Data

(60) Provisional application No. 62/203,777, filed on Aug. 11, 2015.

(51) Int. Cl.
*G16H 10/20* (2018.01)
*G16H 50/20* (2018.01)
*G16H 50/30* (2018.01)
*G16H 50/70* (2018.01)

(52) U.S. Cl.
CPC ............. *G16H 50/20* (2018.01); *G16H 50/30* (2018.01); *G16H 50/70* (2018.01); *A61B 5/168* (2013.01)

(58) Field of Classification Search
CPC ........ G16H 10/20; G16H 50/20; G16H 50/30; G16H 50/70; G16H 10/00–80/00; G06N 3/00–99/007
See application file for complete search history.

(56) References Cited

U.S. PATENT DOCUMENTS

| | | |
|---|---|---|
| 6,186,145 B1 | 2/2001 | Brown |
| 6,380,928 B1* | 4/2002 | Todd ..................... G06Q 30/02 345/169 |
| 6,569,093 B2 | 5/2003 | Iliff |
| 6,957,202 B2 | 10/2005 | Skaanning et al. |
| 7,043,439 B2 | 5/2006 | Jost et al. |
| 7,155,421 B1 | 12/2006 | Haldar |
| 7,311,666 B2 | 12/2007 | Stupp et al. |
| 7,478,064 B1* | 1/2009 | Nacht ..................... G06Q 40/00 705/38 |
| 7,958,066 B2 | 6/2011 | Pinckney et al. |
| 7,974,872 B2 | 7/2011 | Katayama et al. |
| 8,024,332 B2 | 9/2011 | Cao et al. |
| 8,655,817 B2 | 2/2014 | De et al. |
| 8,834,174 B2 | 9/2014 | Malik |
| 9,043,888 B1* | 5/2015 | Ibel ..................... G06Q 50/265 715/745 |
| 9,305,059 B1 | 4/2016 | Glickman et al. |
| 9,443,199 B2 | 9/2016 | Pinckney et al. |
| 9,443,205 B2 | 9/2016 | Wall |
| 9,916,628 B1* | 3/2018 | Wang ..................... G06Q 40/123 |
| 10,052,057 B2 | 8/2018 | Klin et al. |
| 10,311,645 B1 | 6/2019 | Ravindran et al. |
| 10,478,112 B2 | 11/2019 | Wall |
| 10,687,751 B2 | 6/2020 | Wall |
| 10,839,950 B2 | 11/2020 | Vaughan |
| 10,874,355 B2 | 12/2020 | Vaughan et al. |
| 11,024,422 B2 | 6/2021 | Wall |
| 11,176,444 B2 | 11/2021 | Wall et al. |
| 2001/0034615 A1 | 10/2001 | Wilkinson et al. |
| 2001/0036444 A1 | 11/2001 | Placke et al. |
| 2002/0019747 A1* | 2/2002 | Ware ..................... G16H 50/20 705/2 |
| 2002/0035486 A1 | 3/2002 | Huyn et al. |
| 2002/0042786 A1 | 4/2002 | Scarborough et al. |
| 2002/0055916 A1* | 5/2002 | Jost ..................... G06F 16/90332 700/83 |
| 2002/0091563 A1* | 7/2002 | Wasa ..................... G06Q 30/0203 705/7.32 |
| 2003/0032069 A1 | 2/2003 | Muraca |
| 2003/0191680 A1 | 10/2003 | Dewar |
| 2004/0015337 A1 | 1/2004 | Thomas et al. |
| 2004/0103001 A1 | 5/2004 | Mazar et al. |
| 2004/0147840 A1 | 7/2004 | Duggirala et al. |
| 2004/0197750 A1 | 10/2004 | Donaher et al. |
| 2004/0210159 A1 | 10/2004 | Kibar |
| 2004/0265784 A1 | 12/2004 | Stout |
| 2005/0075887 A1 | 4/2005 | Bernard et al. |
| 2005/0142524 A1 | 6/2005 | Simon et al. |
| 2005/0176057 A1 | 8/2005 | Bremer et al. |
| 2005/0187802 A1 | 8/2005 | Koeppel |
| 2005/0197988 A1 | 9/2005 | Bublitz |
| 2005/0209785 A1 | 9/2005 | Wells et al. |
| 2005/0216243 A1 | 9/2005 | Graham et al. |
| 2005/0260549 A1 | 11/2005 | Feierstein et al. |
| 2006/0009683 A1 | 1/2006 | Sakai et al. |
| 2006/0059145 A1 | 3/2006 | Henschke et al. |
| 2006/0078856 A1 | 4/2006 | Kellman |
| 2006/0282306 A1 | 12/2006 | Thissen-Roe |
| 2007/0118399 A1 | 5/2007 | Avinash et al. |
| 2007/0207449 A1* | 9/2007 | Feierstein ................ G09B 7/02 434/323 |
| 2008/0014566 A1 | 1/2008 | Chapman et al. |
| 2008/0016024 A1 | 1/2008 | Andoh et al. |
| 2008/0052318 A1* | 2/2008 | Iliff ..................... G16H 50/20 |
| 2009/0007924 A1* | 1/2009 | Iliff ..................... G16H 50/20 600/300 |
| 2009/0016559 A1 | 1/2009 | Cleary |
| 2009/0083075 A1 | 3/2009 | Henschke et al. |
| 2009/0124886 A1 | 5/2009 | Wang et al. |
| 2009/0137923 A1 | 5/2009 | Suffin et al. |
| 2009/0182578 A1 | 7/2009 | Ozersky |
| 2009/0259494 A1 | 10/2009 | Feder et al. |
| 2010/0023346 A1 | 1/2010 | Paty et al. |
| 2010/0068687 A1 | 3/2010 | Bertelsen |
| 2010/0088259 A1* | 4/2010 | Valpola ..................... G06N 3/08 706/14 |
| 2010/0094560 A1* | 4/2010 | Lois ..................... G01N 33/564 702/179 |
| 2010/0177950 A1 | 7/2010 | Donovan et al. |
| 2010/0179928 A1 | 7/2010 | Hodgin |
| 2010/0184093 A1 | 7/2010 | Donovan et al. |
| 2010/0189818 A1 | 7/2010 | Tsai |
| 2010/0234691 A1* | 9/2010 | Iwano ..................... G16H 10/20 600/300 |
| 2010/0280760 A1 | 11/2010 | Pi et al. |
| 2010/0332430 A1 | 12/2010 | Caraviello et al. |
| 2011/0082712 A1 | 4/2011 | Eberhardt, III et al. |
| 2011/0119212 A1 | 5/2011 | De Bruin et al. |
| 2011/0145161 A1 | 6/2011 | Scarborough et al. |
| 2011/0184379 A1 | 7/2011 | Van Antwerp et al. |
| 2011/0218253 A1 | 9/2011 | Lange et al. |
| 2012/0004925 A1 | 1/2012 | Braverman et al. |
| 2012/0028816 A1 | 2/2012 | Warren et al. |
| 2012/0059282 A1 | 3/2012 | Agichtein et al. |
| 2012/0101852 A1 | 4/2012 | Albert |
| 2012/0102405 A1* | 4/2012 | Zuckerman ............ G16H 50/20 715/733 |
| 2012/0108909 A1 | 5/2012 | Slobounov et al. |
| 2012/0183128 A1* | 7/2012 | Clawson ............ H04M 3/5116 379/45 |
| 2012/0270199 A1 | 10/2012 | Malik |
| 2013/0117280 A1* | 5/2013 | Donaldson ............ G06F 16/17 707/754 |
| 2013/0159010 A1 | 6/2013 | Paty et al. |
| 2013/0178731 A1 | 7/2013 | Bosl |
| 2013/0184603 A1 | 7/2013 | Rothman |
| 2013/0262357 A1 | 10/2013 | Amarasingham et al. |
| 2013/0267441 A1 | 10/2013 | Momeni et al. |
| 2013/0268203 A1* | 10/2013 | Pyloth ..................... G16H 50/20 702/19 |
| 2014/0006319 A1 | 1/2014 | Anand et al. |
| 2014/0052474 A1 | 2/2014 | Madan et al. |
| 2014/0057241 A1* | 2/2014 | Rapp ..................... G09B 7/02 434/353 |
| 2014/0063236 A1 | 3/2014 | Shreve et al. |
| 2014/0074848 A1 | 3/2014 | Kettunen et al. |
| 2014/0122109 A1* | 5/2014 | Ghanbari ............ G16H 10/20 705/2 |
| 2014/0141983 A1 | 5/2014 | Singh et al. |
| 2014/0143325 A1* | 5/2014 | Lessin ..................... H04L 67/306 709/204 |
| 2014/0148728 A1 | 5/2014 | Eizenman et al. |
| 2014/0219986 A1 | 8/2014 | Greene et al. |
| 2014/0223462 A1 | 8/2014 | Aimone et al. |
| 2014/0253876 A1 | 9/2014 | Klin et al. |
| 2014/0279746 A1 | 9/2014 | De Bruin et al. |
| 2014/0304200 A1 | 10/2014 | Wall |

(56) References Cited

U.S. PATENT DOCUMENTS

| | | | |
|---|---|---|---|
| 2014/0309270 A1* | 10/2014 | Price | A61P 25/00 514/738 |
| 2014/0330576 A1 | 11/2014 | Bauer | |
| 2014/0330618 A1* | 11/2014 | Wong | G06Q 30/0203 705/7.32 |
| 2014/0335499 A1* | 11/2014 | Miele | G09B 7/08 434/353 |
| 2014/0336539 A1 | 11/2014 | Torres et al. | |
| 2014/0343450 A1 | 11/2014 | Stack | |
| 2015/0004588 A1 | 1/2015 | Vats et al. | |
| 2015/0006192 A1 | 1/2015 | Sudharsan et al. | |
| 2015/0066520 A1* | 3/2015 | Leon | G16H 10/20 705/2 |
| 2015/0080671 A1 | 3/2015 | Christensen et al. | |
| 2015/0099946 A1 | 4/2015 | Sahin | |
| 2015/0119437 A1 | 4/2015 | Clark et al. | |
| 2015/0154372 A1 | 6/2015 | Soenksen et al. | |
| 2015/0227681 A1* | 8/2015 | Courchesne | G16H 50/20 702/19 |
| 2015/0315182 A1 | 11/2015 | Lee et al. | |
| 2016/0022137 A1 | 1/2016 | Wetzel et al. | |
| 2016/0046990 A1 | 2/2016 | Hensel | |
| 2016/0135706 A1 | 5/2016 | Sullivan et al. | |
| 2016/0140323 A1* | 5/2016 | Jiao | G16H 10/20 705/2 |
| 2016/0140642 A1* | 5/2016 | Jiao | G06Q 30/0631 705/2 |
| 2016/0140859 A1 | 5/2016 | Jiao et al. | |
| 2016/0148093 A1* | 5/2016 | Adderly | G06N 5/022 706/46 |
| 2016/0148114 A1* | 5/2016 | Allen | G06N 5/02 706/11 |
| 2016/0180038 A1 | 6/2016 | Clark et al. | |
| 2016/0180248 A1 | 6/2016 | Regan | |
| 2016/0196504 A1* | 7/2016 | Allen | G06N 20/00 706/11 |
| 2016/0203280 A1 | 7/2016 | Neville | |
| 2016/0209428 A1 | 7/2016 | Naviaux et al. | |
| 2016/0232320 A1* | 8/2016 | Sklar | G16H 10/20 |
| 2016/0232328 A1 | 8/2016 | Sklar et al. | |
| 2016/0342756 A1 | 11/2016 | Wall | |
| 2017/0035792 A1 | 2/2017 | Montagnier et al. | |
| 2017/0069216 A1 | 3/2017 | Vaughan et al. | |
| 2017/0091423 A1 | 3/2017 | Kumar et al. | |
| 2017/0160878 A1 | 6/2017 | Endo et al. | |
| 2017/0169178 A1 | 6/2017 | Beehler et al. | |
| 2017/0262609 A1 | 9/2017 | Perlroth et al. | |
| 2017/0365101 A1 | 12/2017 | Samec et al. | |
| 2018/0098724 A1 | 4/2018 | Lu et al. | |
| 2018/0132780 A1 | 5/2018 | Saar | |
| 2018/0184964 A1 | 7/2018 | Simon et al. | |
| 2018/0366144 A1 | 12/2018 | Ashoori et al. | |
| 2019/0019581 A1 | 1/2019 | Vaughan et al. | |
| 2019/0038202 A1 | 2/2019 | Wall | |
| 2019/0043610 A1 | 2/2019 | Vaughan | |
| 2019/0043618 A1 | 2/2019 | Vaughan et al. | |
| 2019/0043619 A1 | 2/2019 | Vaughan et al. | |
| 2019/0088366 A1 | 3/2019 | Vaughan et al. | |
| 2019/0244127 A1 | 8/2019 | Amado et al. | |
| 2021/0133509 A1 | 5/2021 | Wall et al. | |
| 2021/0174919 A1 | 6/2021 | Vaughan | |
| 2021/0335489 A1 | 10/2021 | Wall | |
| 2022/0369976 A1 | 11/2022 | Abbas et al. | |

FOREIGN PATENT DOCUMENTS

| | | | |
|---|---|---|---|
| CN | 101149767 A | 3/2008 | |
| CN | 101499078 A | 8/2009 | |
| CN | 101689220 A | 3/2010 | |
| CN | 101821741 A | 9/2010 | |
| CN | 102663129 A | 9/2012 | |
| CN | 102971755 A | 3/2013 | |
| CN | 103473631 A | 12/2013 | |
| CN | 103493054 A | 1/2014 | |
| CN | 103714261 A | 4/2014 | |
| CN | 104254863 A | 12/2014 | |
| CN | 104504297 A | 4/2015 | |
| EP | 0424869 | 2/1991 | |
| EP | 3941340 A1 | 1/2022 | |
| JP | 2001034688 A | 2/2001 | |
| JP | 2002318858 A | 10/2002 | |
| JP | 2007249878 A | 9/2007 | |
| JP | 2011255106 A | 12/2011 | |
| JP | 2015228202 A | 12/2015 | |
| JP | 2017504087 A | 2/2017 | |
| JP | 2021184816 A | 12/2021 | |
| WO | WO-9521419 A1 | 8/1995 | |
| WO | WO-9705553 A1 | 2/1997 | |
| WO | WO-2008124138 A1 | 10/2008 | |
| WO | WO-2010059709 A2 | 5/2010 | |
| WO | WO-2012082056 A1 | 6/2012 | |
| WO | WO-2013062937 A2 | 5/2013 | |
| WO | WO-2014012144 A1 * | 1/2014 | C12Q 1/6883 |
| WO | WO-2015006364 A2 | 1/2015 | |
| WO | WO-2015058558 A1 * | 4/2015 | G06F 16/9535 |
| WO | WO-2015066203 A2 | 5/2015 | |
| WO | WO-2016110804 A1 | 7/2016 | |
| WO | WO-2017027709 A1 | 2/2017 | |
| WO | WO-2017106770 A1 | 6/2017 | |
| WO | WO-2018090009 A1 | 5/2018 | |
| WO | WO-2018148365 A1 | 8/2018 | |
| WO | WO-2020198065 A1 | 10/2020 | |
| WO | WO-2021046412 A1 | 3/2021 | |

OTHER PUBLICATIONS

Bailey, et al. Autism as a strongly genetic disorder: evidence from a British twin study. Psychol Med. Jan. 1995;25(1):63-77.

Bernier, et al. Psychopathology, families, and culture: autism. Child Adolesc Psychiatr Clin N Am. Oct. 2010;19(4):855-67.

Berument, et al. Autism screening questionnaire: diagnostic validity. Br J Psychiatry. Nov. 1999; 175:444-51.

Breiman et al.: Chapter 6 Medical diagnosis and prognosis. Classification and regression trees. Chappman & Hall/CRC (1984) (pp. 174-346).

Breiman. Random Forests. Machine Learning 45:5-32 (2001).

Canadian Patent Application No. 2,857,069 Office Action dated Jun. 18, 2019.

Cicchetti, et al. Reliability of the ADI-R: multiple examiners evaluate a single case. J Autism Dev Disord. Apr. 2008;38(4):764-70. Epub Dec. 5, 2007.

Cohen. Fast effective rule induction. Proceedings of the Twelfth International Conference on Machine Learning. (pp. 115-123) (1995).

Duda, et al. Clinical Evaluation of a Novel and Mobile Autism Risk Assessment. J Autism Dev Disord. Jun. 2016;46(6):1953-61.

Duda, et al. Testing the accuracy of an observation-based classifier for rapid detection of autism risk Transl Psychiatry. Aug. 12, 2014;4:e424.

Duda, et al. Testing the accuracy of an observation-based classifier for rapid detection of autism risk. Transl Psychiatry. Apr. 28, 2015;5:e556.

Elder et al., Clinical impact of early diagnosis of autism on the prognosis and parent-child relationships. Psychology Research and Behavior Management 10: 283-292 (2017).

EP12844474.2. Search Report and Search Opinion dated Jun. 26, 2015.

European Application No. 18750938.5 Search Report dated Oct. 16, 2020.

European Patent Application No. 16876856.2 Examination Search Report dated Jul. 15, 2019.

Fischbach, et al. The Simons Simplex Collection: a resource for identification of autism genetic risk factors. Neuron. Oct. 21, 2010;68(2):192-5.

Fisher et al., DISC Interviewer Manual. Section 2 Computerized Versions of the DISC (2006).

Frank, et al. A simple approach to ordinal prediction. European conference on Maching Learning; Freiburg, Germany, Springer-Verlag 2001:145-156.

(56) References Cited

OTHER PUBLICATIONS

Frank, et al. Data mining in bioinformatics using Weka. Bioinformatics. Oct. 12, 2004;20(15):2479-81. Epub Apr. 8, 2004.
Frank et al. Generating accurate rule sets without global optimization. In: Machine Learning: Proceedings of the Fifteenth International Conference: 1998; San Francisco, CA, Morgan Kaufmann Publishers (8 pgs).
Freund, et al. A decision-theoretic generalization of on-line learning and an application to boosting. Journal of computer and system sciences 55.1 (1997): 119-139.
Freund, et al. Experiments with a new boosting algorithm. In: Proceedings of the International Conference on Machine Learning: 1996, San Francisco, Morgan Kautinann: pp. 148-156.
Freund, et al. The alternating decision tree learning algorithm. In: Machine Learning: Proceedings of the Sixteenth International Conference. 1999, pp. 124-133.
Fusaro, et al. The potential of accelerating early detection of autism through content analysis of YouTube videos. PLoS One. Apr. 16, 2014;9(4):e93533.
Gaines, et al. Induction of ripple-down rules applied to modeling large databases. Journal of Intelligent Information Systems 5.3 (1995): 211-228.
GAMA. Functional trees. Machine Learning 55:219-250 (2004).
Geschwind et al. The autism genetic resource exchange: a resource for the study of autism and related neuropsychiatric conditions. The American Journal of Human Genetics 69:463-466 (2001).
Gillberg et al. Early detection of autism. Diagnostic instruments for clinicians. European Child & Adolescent Psychiatry 5.2:67-74. (1996).
Golarai, G. et al. Autism and the development of face processing. Clinical Neuroscience Research 6:145-160 (2006).
Gotham, et al. The Autism Diagnostic Observation Schedule: revised algorithms for improved diagnostic validity. J Autism Dev Disord. Apr. 2007;37(4):613-27. Epub Dec. 16, 2006.
Gura, et al. Autism spectrum disorder screening in primary care. J Dev Behav Pediatr. Jan. 2011;32(1):48-51.
Hall et al. The WEKA data mining software: an update. SIGKDD Explorations Newsletter 11:10-18 (2009).
Hamidpour, et al., Antipurinergic therapy with Suramin as a treatment for autism spectrum disorder, Journal of Biomedical sciences, Mar. 29, 2016; 5:pp. 17; abstract, p. 1, p. 2, p. 4, p. 5.
Hirsch, S. et al. Development of a questionnaire weighted scoring system to target diagnostic examinations for asthma in adults: a modelling study. BMC Fam. Pract. 5:30 pp. 1-13 (2004) [E-pub Dec. 17, 2004].
Holmes et al. Multiclass alternating decision trees. Machine learning: ECML 2002. Springer Berlin Heidelberg, (pp. 161-172) (2002).
Holte. Very simple classification rules perform well on most commonly used datasets. Machine learning 11:63-91 (1993).
Howlin. Chapter 3—Identifying and assessing children with autism or asperger syndrome. Children with Autism and Asperger's Syndrome: A Guide for Practitioners and Carers. UK: John Wiley and Sons (1998) (pp. 52-75, 294-321).
Kobak et al. Web-based training in early autism screening: results from a pilot study. Telemed JE Health. Oct. 2011;17(8):640-4.
Kohavi. A study of cross-validation and bootstrap for accuracy estimation and model selection. In: Proceedings IJCAI-95: 1995: Montreal, Morgan Kaufmann, Los Altos, CA: 1137-1143.
Kosmicki, et al. Searching for a minimal set of behaviors for autism detection through feature selection-based machine learning. Transl Psychiatry. Feb. 24, 20154;5:e514.
Landwehr et al. Logistic model trees. Machine Learning 59:161-205 (2005).
Lord et al. Autism Diagnostic Interview-Revised: A revised version of a diagnostic interview for caregivers of individuals with possible pervasive developmental disorders. J Autism Dev Discord 24(5):659-685 (1994).
Lord, et al. Autism diagnostic observation schedule: a standardized observation of communicative and social behavior. J Autism Dev Disord. Jun. 1989; 19(2):185-212.
Lord et al. The Autism Diagnostic Observation Schedule-Generic: A Standard Measure of Social and Communication Deficits Associated with the Spectrum of Autism. J Autism Dev Discord 30(3):205-223 (2000).
Martin. Instance-Based learning: Nearest neighbor with generalization. Hamilton, New Zealand, University of Waikato (83 pgs) (1995).
Mayes et al., Autism and ADHD: Overlapping and discriminating symptoms. Research in Autism Spectrum Disorders 6(1) :277-285 (2012).
Moore et al. Cached Sufficient Statistics for Efficient Machine Learning with Large Datasets. JAIR 8:67-91 (1998).
Muangnak et al. Classification students with learning disabilities using naive bayes classifier and decision tree. The 6th International Conference on Networked Computing and Advanced Information Management. IEEE, 2010.
Ogden, et al., Suramin as a chemosensitizer: Oral pharmacokinetics in rats, Pharmaceutical research, Nov. 2004;21:2058-2063; p. 2058.
Ordonez, C. et al. Machine learning techniques applied to the determination of osteoporosis incidence in post-menopausal women. Mathematical and Computer Modelling, 50:673-679 (2009).
PCT/US2012/061422 International Search Report and Written Opinion dated May 24, 2013.
PCT/US2016/046557 International Search Report and Written Opinion dated Nov. 3, 2016.
PCT/US2016/067358 International Preliminary Report on Patentability dated Jun. 28, 2018.
PCT/US2016/067358 International Search Report and Written Opinion dated Apr. 13, 2017.
PCT/US2017/061552 International Search Report and Written Opinion dated Mar. 26, 2018.
PCT/US2018/017354 International Preliminary Report on Patentability dated Aug. 13, 2019.
PCT/US2018/017354 International Search Report and Written Opinion dated Apr. 26, 2018.
PCT/US2020/049492 International Search Report and Written Opinion dated Dec. 10, 2020.
PCT/US2020/053611 International Search Report and Written Opinion dated Dec. 21, 2020.
Pinto-Martin, et al. Screening strategies for autism spectrum disorders in pediatric primary care. J Dev Behav Pediatr. Oct. 2008;29(5):345-50.
Pisula, E. Parents of children with autism: review of current research. Arch Psychiatry Psychother, 2003, 5: 51-63.
Plajner et al., Bayesian Network Models for Adaptive Testing; Proceedings of the Twelfth Bayesian Modeling Applications Workshop, co-located with the 31st Conference on Uncertainty in Artificial Intelligence; Amsterdam, The Netherlands, Jul. 16, 2015; http://ceur-ws.org/Vol-1565/ (Year: 2015).
Planjner, Slide presentation on Bayesian Network Models for Adaptive Testing: Proceeding of the Twelfth Bayesian Modeling Applications Workshop (2015).
Quinlan. C4. 5: Programming for machine learning. Morgan Kaufmann (6 pgs) (1993).
Risi, et al. Combining information from multiple sources in the diagnosis of autism spectrum disorders. Journal of the American Academy of Child & Adolescent Psychiatry, 2006, 45(9):1094-1103.
Robins, et al. The Modified Checklist for Autism in Toddlers: an initial study investigating the early detection of autism and pervasive developmental disorders. J Autism Dev Disord. Apr. 2001;31(2):131-44.
Rutter et al. Autism diagnostic interview-revised. Los Angeles, CA: Western Psychological Services 29:30 (2003).
Santosh et al. The construction and validation of a short form of the developmental, diagnostic and dimensional interview. Eur Child Adolesc Psychiatry. Aug. 2009;18(8):521-4.
Shattuck, et al. Timing of identification among children with an autism spectrum disorder: findings from a population-based surveillance study. J Am Acad Child Adolesc Psychiatry. May 2009;48(5):474-83.
Shi. Best-first decision tree learning. Master Thesis, The University of Waikato (120 pgs) (2007).

(56) References Cited

OTHER PUBLICATIONS

Skuse et al. The developmental, dimensional and diagnostic interview (3di): a novel computerized assessment for autism spectrum disorders. Journal of the American Academy of Child & Adolescent Psychiatry 43.5:548-558 (2004).
Tadevosyan-Leyfer, et al. A principal components analysis of the Autism Diagnostic Interview-Revised. J Am Acad Child Adolesc Psychiatry. Jul. 2003;42(7):864-72.
U.S. Appl. No. 16/155,794 Office Action dated Aug. 15, 2019.
U.S. Appl. No. 16/155,798 Office Action dated Jul. 29, 2019.
U.S. Appl. No. 16/010,284 Non-Final Office Action dated Feb. 4, 2021.
U.S. Appl. No. 16/155,758 Final Office Action dated Jan. 12, 2021.
U.S. Appl. No. 15/234,814 Non-Final Office Action dated Mar. 24, 2020.
U.S. Appl. No. 15/234,814 Office Action dated Oct. 3, 2019.
U.S. Appl. No. 16/155,761 Non-Final Office Action dated Apr. 2, 2020.
U.S. Appl. No. 16/155,761 Office Action dated Oct. 7, 2019.
U.S. Appl. No. 16/155,794 Non-Final Office Action dated Apr. 16, 2020.
U.S. Appl. No. 16/155,798 Non-Final Office Action dated Apr. 9, 2020.
U.S. Appl. No. 14/354,032 Notice of Allowance dated Apr. 13, 2016.
U.S. Appl. No. 14/354,032 Notice of Allowance dated Jun. 14, 2016.
U.S. Appl. No. 14/354,032 Office Action dated Jul. 28, 2015.
U.S. Appl. No. 15/234,814 Non-Final Office Action Mailed Jun. 7, 2018.
U.S. Appl. No. 15/234,814 Office Action dated Jan. 18, 2019.
U.S. Appl. No. 16/155,758 Preinterview First Office Action dated Feb. 8, 2019.
U.S. Appl. No. 16/155,761 Preinterview First Office Action dated Jan. 9, 2019.
U.S. Appl. No. 16/155,794 Office Action dated Jan. 14, 2019.
U.S. Appl. No. 16/157,787 Office Action dated Mar. 27, 2019.
Van Stralen et al. Diagnostic methods I: sensitivity, specificity, and other measures of accuracy. Kidney Int. 75(12):1257-1263 (2009).
Wall et al. Use of artificial intelligence to shorten the behavioral diagnosis of autism. PLoS One. 2012;7(8):e43855.
Wall, et al. Use of machine learning to shorten observation-based screening and diagnosis of autism. Transl Psychiatry. Apr. 10, 2012;2:e100.
Wenner, M. Gut Bacteria May Play a Role in Autism. Scientific American, pp. 1-4, Sep. 1, 2014.
Wiggins, et al. Examination of the time between first evaluation and first autism spectrum diagnosis in a population-based sample. J Dev Behav Pediatr. Apr. 2006;27(2 Suppl):S79-87.
Witten et al. Data Mining: Practical Machine Learning Tools and Techniques with Java Implementations. Morgan Kaufmann, Amsterdam, Second Edition (558 pgs) (Oct. 2005).
Artoni, et al. Accessible Education for Autistic Children: ABA-based Didactic Software. International Conference on Universal Access in Human-Computer Interaction (2011): 11 pages.
Atherton, et al. Autism Through the Ages: A Mixed Methods Approach to Understanding How Age and Age of Diagnosis Affect Quality of Life. Journal of Autism and Developmental Disorders (2021): 16 pages.
European Patent Application No. 16835913.1 Communication pursuant to Article 94(3) dated Feb. 28, 2022.
European Patent Application No. 16835913.1 Extended European Search Report dated Mar. 29, 2019.
Golarai, et al. Autism and the Development of Face Processing. Clinical Neuroscience Research. vol. 6 Issue. 3 (2006): 16 pages.
Moyer. Gut Bacteria May Play a Role in Autism. Scientific American (2014): 4 pages.
Sok, et al. Multivariate Alternating Decision Trees. Pattern Recognition. vol. 50, (2016): 15 pages.
U.S. Appl. No. 15/930,998 Notice of Allowance dated Apr. 22, 2021.
U.S. Appl. No. 15/930,998 Office Action dated Sep. 15, 2020.
U.S. Appl. No. 16/157,787 Corrected Notice of Allowability dated Oct. 2, 2019.
U.S. Appl. No. 16/157,787 Notice of Allowance dated Aug. 30, 2019.
U.S. Appl. No. 17/690,977 Office Action dated Jan. 4, 2023.
U.S. Appl. No. 17/690,977 Office Action dated Sep. 14, 2022.
Ward, et al. The Autistic Behavioural Indicators Instrument (ABII): Development and Instrument Utility in Discriminating Autistic Disorder From Speech and Language Impairment and Typical Development. Research in Autism Spectrum Disorders. vol. 4 (2010): 15 pages.
Witten, et al. Weka: Practical Machine Learning Tools and Techniques with Java Implementations. University of Waikato, Department of Computer Science. (1999): 4 pages.

* cited by examiner

METHODS AND APPARATUS TO DETERMINE DEVELOPMENTAL PROGRESS WITH ARTIFICIAL INTELLIGENCE AND USER INPUT

CROSS-REFERENCE

This application is a continuation application of Ser. No. 15/234,814, filed Aug. 11, 2016, which claims priority to U.S. Provisional Application Ser. No. 62/203,777, filed on Aug. 11, 2015, which applications are incorporated herein by reference.

The subject matter of the present application is also related to U.S. application Ser. No. 14/354,032, filed on Apr. 24, 2014, published as U.S. Patent Publication No. US2014/0304200A1 on Oct. 9, 2014, now U.S. Pat. No. 9,443,205, issued Sep. 13, 2016, entitled "Enhancing Diagnosis of Disorder Through Artificial Intelligence and Mobile Health Technologies Without Compromising Accuracy", each of which is incorporated herein by reference in its entirety.

BACKGROUND OF THE INVENTION

Prior methods and apparatus for diagnosing people with a developmental disorder can be less than ideal in at least some respects. Unfortunately, a less than ideal amount of time, energy and money can be required to obtain a diagnosis or determine whether a subject is at risk for developmental disorders such as autism, autistic spectrum, attention deficit disorder, attention deficit hyperactive disorder and speech and learning disability, for example. The healthcare system is under increasing pressure to deliver care at lower costs, and prior methods and apparatus for clinically diagnosing or identifying a subject as at risk of a developmental disorder can result in greater expense and burden on the health care system than would be ideal. Further, at least some subjects are not treated as soon as ideally would occur, such that the burden on the healthcare system is increased with the additional care required for these subjects.

The identification of developmental disorders in subjects presents a daunting technical problem in terms of both accuracy and efficiency. Many known methods for identifying such disorders are often time-consuming and resource-intensive, requiring a subject to answer a large number of questions or undergo extensive observation under the administration of qualified clinicians, who may be limited in number and availability depending on the subject's geographical location. In addition, many known methods for identifying developmental disorders have less than ideal accuracy and consistency, as subjects to be evaluated using such methods often present a vast range of variation that can be difficult to capture and classify. A technical solution to such a technical problem would be desirable, wherein the technical solution can improve both the accuracy and efficiency of existing methods. Ideally, such a technical solution would reduce the required time and resources for administering a method for identifying developmental disorders, and improve the accuracy and consistency of the identification outcomes across subjects.

Although prior lengthy tests with questions can be administered to caretakers such as parents in order to diagnose or identify a subject as at risk for a developmental disorder, such tests can be quite long and burdensome. For example at least some of these tests have over one hundred questions, and more than one such lengthy test may be administered further increasing the burden on health care providers and caretakers. Additional data may be required such as clinical observation of the subject, and clinical visits may further increase the amount of time and burden on the healthcare system. Consequently, the time between a subject being identified as needing to be evaluated and being clinically identified as at risk or diagnosed with a developmental delay can be several months, and in some instances over a year.

The delay between identified need for an evaluation and clinical diagnosis can result in less than ideal care in at least some instances. Some developmental disorders can be treated with timely intervention. However, the large gap between a caretaker initially identifying a prospective as needing an evaluation and clinically diagnosing the subject or clinically identifying the subject as at risk can result in less than ideal treatment. In at least some instances, a developmental disorder may have a treatment window, and the treatment window may be missed or the subject treated for only a portion of the treatment window.

Although prior methods and apparatus have been proposed to decrease the number of questions asked, such prior methods and apparatus can be less than ideal in at least some respects. Although prior methods and apparatus have relied on training and test datasets to train and validate, respectively, the methods and apparatus, the actual clinical results of such methods and apparatus can be less than ideal, as the clinical environment can present more challenging cases than the training and test dataset. The clinical environment can present subjects who may have one or more of several possible developmental disorders, and relying on a subset of questions may result in less than ideal sensitivity and specificity of the tested developmental disorder. Also, the use of only one test to diagnose only one developmental disorder, e.g. autism, may provide less than ideal results for diagnosing the intended developmental disorder and other disorders, as subject behavior from other developmental disorders may present confounding variables that decrease the sensitivity and specificity of the subset of questions targeting the one developmental disorder. Also, reliance on a predetermined subset can result in less than ideal results as more questions than would be ideal may be asked, and the questions asked may not be the ideal subset of questions for a particular subject.

Further, many subjects may have two or more related disorders or conditions. If each test is designed to diagnose or identify only a single disorder or condition, a subject presenting with multiple disorders may be required to take multiple tests. The evaluation of a subject using multiple diagnostic tests may be lengthy, expensive, inconvenient, and logistically challenging to arrange. It would be desirable to provide a way to test a subject using a single diagnostic test that is capable of identifying or diagnosing multiple related disorders or conditions with sufficient sensitivity and specificity.

In light of the above, improved methods and apparatus of diagnosing and identifying subjects at risk are needed. Ideally such methods and apparatus would require fewer questions, decreased amounts of time, determine a plurality of developmental disorders, and provide clinically acceptable sensitivity and specificity in a clinical or nonclinical environment. Ideally, such methods and apparatus can also be used to determine the developmental progress of a subject.

SUMMARY OF THE INVENTION

The methods and apparatus disclosed herein can determine the developmental progress of a subject in a clinical or nonclinical environment. For example, the described methods and apparatus can identify a subject as developmentally advanced in one or more areas of development, or identify a subject as developmentally delayed or at risk of having one or more developmental disorders. The methods and apparatus disclosed can determine the subject's developmental progress by analyzing a plurality of characteristics or features of the subject based on an assessment model, wherein the assessment model can be generated from large datasets of relevant subject populations using machine-learning approaches. The methods and apparatus disclosed herein comprise improved logical structures and processes to diagnose a subject with a disorder among a plurality of disorders, using a single test.

The methods and apparatus disclosed herein can diagnose or identify a subject as at risk of having one or more developmental disorders among a plurality of developmental disorders in a clinical or nonclinical setting, with fewer questions, in a decreased amounts of time, and with clinically acceptable sensitivity and specificity in a clinical environment. A processor can be configured with instructions to identify a most predictive next question, such that a person can be diagnosed or identified as at risk with fewer questions. Identifying the most predictive next question in response to a plurality of answers has the advantage of increasing the sensitivity and the specificity with fewer questions. The methods and apparatus disclosed herein can be configured to evaluate a subject for a plurality of related developmental disorders using a single test, and diagnose or determine the subject as at risk of one or more of the plurality of developmental disorders using the single test. Decreasing the number of questions presented can be particularly helpful where a subject presents with a plurality of possible developmental disorders. Evaluating the subject for the plurality of possible disorders using just a single test can greatly reduce the length and cost of the evaluation procedure. The methods and apparatus disclosed herein can diagnose or identify the subject as at risk for having a single developmental disorder among a plurality of possible developmental disorders that may have overlapping symptoms.

While the most predictive next question can be determined in many ways, in many instances the most predictive next question is determined in response to a plurality of answers to preceding questions that may comprise prior most predictive next questions. The most predictive next question can be determined statistically, and a set of possible most predictive next questions evaluated to determine the most predictive next question. In many instances, answers to each of the possible most predictive next questions are related to the relevance of the question, and the relevance of the question can be determined in response to the combined feature importance of each possible answer to a question.

In one aspect, disclosed herein is an apparatus for evaluating a subject for risk of having a developmental disorder among two or more related developmental disorders. The apparatus comprises a processor comprising a tangible medium configured with instructions to present a question to the subject, the question configured to assess a clinical characteristic related to the two or more related developmental disorders. The tangible medium is further configured with instructions to receive an answer corresponding to the clinical characteristic of the subject related to the two or more related developmental disorders. The tangible medium is further configured with instructions to determine, in response to the answer, whether the subject is at greater risk of a first developmental disorder or a second developmental disorder of the two or more related developmental disorders, with a sensitivity and specificity of at least 80%.

In another aspect, disclosed herein is an apparatus for evaluating a subject for risk of having a developmental disorder among two or more related developmental disorders. The apparatus comprises a processor comprising a tangible medium having an assessment model stored thereon, the assessment model comprising statistical correlations among a plurality of clinical characteristics and clinical diagnoses of the two or more related developmental disorders. The tangible medium is configured with instructions to receive an answer corresponding to a clinical characteristic of the subject related to the two or more related developmental disorders. The tangible medium is further configured with instructions to determine, in response to the answer and the assessment model, whether the subject is at greater risk of a first developmental disorder or a second developmental disorder of the two or more related developmental disorders, in response to the assessment model.

In another aspect, disclosed herein is an apparatus for evaluating a subject for risk of having a developmental disorder among two or more related developmental disorders having a comorbidity. The apparatus comprises a processor comprising a tangible medium configured with instructions to present a question to the subject, the question configured to assess a clinical characteristic related to the two or more related developmental disorders. The tangible medium is further configured with instructions to receive an answer corresponding to the clinical characteristic of the subject related to the two or more related developmental disorders. The tangible medium is further configured with instructions to determine, in response to the answer, whether the subject is at risk of a first developmental disorder and a second developmental disorder of the two or more related developmental disorders with comorbidity, with a sensitivity and specificity of at least 80%.

In another aspect, disclosed herein is an apparatus for evaluating a subject for risk of having a developmental disorder among two or more related developmental disorders. The apparatus comprises a processor comprising a tangible medium configured with instructions to receive a plurality of answers to a plurality of asked questions among a plurality of questions. The plurality of answers corresponds to clinical characteristics of the subject related to the two or more related developmental disorders. A plurality of remaining unasked questions of the plurality of questions comprises a most predictive next question. The tangible medium is further configured with instructions to determine, based on the plurality of answers, whether the subject is at greater risk of a first developmental disorder or a second developmental disorder of the two or more developmental disorders. The tangible medium is further configured with instructions to identify the most predictive next question among the plurality of remaining unasked questions, in response a determination of the subject as at greater risk of a first developmental disorder or a second developmental disorder of the two or more related developmental disorders.

A question that is most predictive of the first developmental disorder may be identified as the most predictive next question in response to a determination of the subject as at greater risk of the first developmental disorder. A question that is most predictive of the second developmental disorder may be identified as the most predictive next question in response to a determination of the subject as at greater risk of the second developmental disorder.

The processor may be configured with instructions to display the question and the most predictive next question. The processor may comprise instructions to identify the most predictive next question in response to the plurality of answers corresponding to the plurality of clinical characteristics of the subject. The plurality of answers may comprise a sequence of answers to a sequence of most predictive next questions.

The processor may be configured with instructions to identify the most predictive next question in response to an estimated predictive utility of each remaining question. The estimated predictive utility of each remaining question may be determined in response to a combination of a predictive utility of each possible answer to each remaining question and a probability of said each possible answer. The estimated predictive utility of each remaining question may be determined with a summation of products comprising the predictive utility of each possible answer to each remaining question combined with the probability of said each possible answer. The predictive utility of each possible answer may be multiplied by a probability of occurrence for said each possible answer. The predictive utility of each possible answer may correspond to a correlation of said each possible answer with clinical diagnosis of the first developmental disorder. The probability of said each possible answer may be determined in response to one or more answers of the subject corresponding to one or more clinical characteristics of the subject.

The processor may be configured with sufficient statistics to identify the most predictive next question that is most predictive of the first developmental disorder. The sufficient statistics may comprise sufficient statistics determined with one or more of a binary tree, a random forest, a decision tree, a plurality of decision trees, a plurality of decision trees with controlled variance, a multinomial logistic regression, a naive Bayes classifier, a linear classifier, an ensemble of linear classifiers, a boosting algorithm, a boosting algorithm trained with stochastic gradient descent, a boosting algorithm comprising training data weighting, a boosting algorithm comprising updating training data weighting, or a boosting algorithm comprising updating misclassified training data with higher weights. The sufficient statistics may comprise sufficient statistics of a classifier trained and validated on one or more subject populations. The processor may comprise instructions to identify the most predictive next question in response to a plurality of answers corresponding to a plurality of clinical characteristics of the subject, a plurality of remaining questions, and an informativeness of each question of the plurality of remaining questions determined with the sufficient statistics. The most predictive next question may be identified in response to one or more of an informativeness or an estimated predictive utility of the most predictive next question determined in response to a plurality of answers corresponding to a plurality of clinical characteristics of the subject. The processor may comprise instructions to determine an informativeness of the most predictive next question in response to an output of a probabilistic graphical model comprising estimates of probability coefficients determined with logistic regression.

The processor may be configured with sufficient statistics of a machine learning algorithm configured in response to a plurality of clinically assessed subject populations in order to identify the most predictive next question that is most predictive of greater risk of the first developmental disorder. The processor may be configured with instructions to identify the most predictive next question in response to an estimated predictive utility of the most predictive next question with respect to each of the two or more developmental disorders. The processor may be configured with instructions to identify the next most predictive question with one or more of a binary tree, a random forest, a decision tree, a plurality of decision trees, a plurality of decision trees with controlled variance, a multinomial logistic regression, a naive Bayes classifier, a linear classifier, or an ensemble of linear classifiers.

The processor may be configured with instructions to identify first a first plurality of next most predictive questions of a first disorder, and to identify second a second plurality of next most predictive questions of a second disorder in response to a first plurality of answers to the first plurality of next most predictive questions related to the first disorder. The processor may be configured to identify each of the plurality of next most predictive questions in response to an answer to an immediately preceding next most predictive question. The processor may be configured with instructions to determine a first plurality of next most predictive questions together and to receive answers to the first plurality of next most predictive questions, and the processor may be configured to determine a second plurality of next most predictive questions together in response to the answers to the first plurality of next most predictive questions.

The processor may be configured with instructions to determine a first plurality of next most predictive questions of a first disorder and a second plurality of next most predictive questions of a second disorder. The processor may be configured with instructions to determine the second plurality of next most predictive questions of the second disorder in response to answers to the first plurality of next most predictive questions. The processor may be configured with instructions to determine a next most predictive question of the second plurality of next most predictive questions of the second disorder in response to first answers to the first plurality of next most predictive questions and second answers to the second plurality of next most predictive questions. The processor may be configured with instructions to determine a first feature importance related to the first disorder for each of the first plurality of next most predictive questions and a second feature importance related to the second disorder for each of the second plurality of next most predictive questions. The processor may be configured with instructions to determine a next most predictive question of a first disorder and a second disorder.

In another aspect, disclosed herein is an apparatus to determine developmental progress of a subject in response to a plurality of questions. The apparatus comprises a processor comprising a tangible medium configured with instructions to receive a plurality of answers to a plurality of asked questions among a plurality of questions. The plurality of answers correspond to clinical characteristics of the subject related to the developmental progress, and a plurality of remaining unasked questions of the plurality of questions comprise a most predictive next question. The tangible medium is further configured with instructions to determine the developmental progress of the subject based on the plurality of answers. The tangible medium is further configured with instructions to identify the most predictive next question among the plurality of remaining unasked questions, in response to a determination of the developmental progress of the subject.

In another aspect, disclosed herein is an apparatus for evaluating a subject as developmentally advanced in an area of development among a plurality of areas of development. The apparatus comprises a processor comprising a tangible medium configured with instructions to receive a plurality of answers to a plurality of asked questions among a plurality of questions. The plurality of answers correspond to clinical characteristics of the subject related to the plurality of areas of development, and a plurality of remaining unasked questions of the plurality of questions comprise a most predictive next question. The tangible medium is further configured with instructions to determine, based on the plurality of answers, whether the subject is developmentally advanced in a first area of development compared to a second area of development of the plurality of areas of development. The tangible medium is further configured with instructions to identify the most predictive next question among the plurality of remaining unasked questions, in response a determination of the subject as developmentally advanced in the first area of development compared to the second area of development of the plurality of areas of development.

In another aspect, disclosed herein is an apparatus for evaluating a subject for risk of having a developmental disorder among two or more developmental disorders. The apparatus comprises a processor comprising a tangible medium configured with instructions to receive input data corresponding a clinical characteristic of the subject related to the two or more developmental disorders. The tangible medium is further configured with instructions to determine, in response to the input data, whether the subject is at greater risk of a first developmental disorder or a second developmental disorder of the two or more related developmental disorders, with a sensitivity and specificity of at least 80%.

In another aspect, disclosed herein is an apparatus for evaluating a subject for risk of having a developmental disorder among two or more related developmental disorders. The apparatus comprises a memory having an assessment model stored thereon, the assessment model comprising statistical correlations between a plurality of clinical characteristics and clinical diagnoses of the two or more related developmental disorders. The apparatus further comprises a processor comprising a tangible medium configured with instructions to receive input data corresponding a clinical characteristic of the subject related to the two or more developmental disorders. The tangible medium is further configured with instructions to determine, in response to the input data and the assessment model, whether the subject is at greater risk of a first developmental disorder or a second developmental disorder of the two or more related developmental disorders.

In another aspect, disclosed herein is an apparatus for evaluating a subject for risk of having a developmental disorder among two or more developmental disorders. The apparatus comprises a processor comprising a tangible medium configured with instructions to receive input data corresponding a first clinical characteristic of the subject related to the two or more developmental disorders. The tangible medium is further configured with instructions to determine, in response to the input data, whether the subject is at greater risk of a first developmental disorder or a second developmental disorder of the two or more related developmental disorders. The tangible medium is further configured with instructions to identify a second clinical characteristic that is most predictive of the first developmental disorder, in response to the determination of the subject as at greater risk of the first developmental disorder. The tangible medium is further configured with instructions to receive additional input data corresponding to the second clinical characteristic of the subject.

The input data may comprise one or more of an answer of the subject to a question, a result of a structured interaction with the subject, a performance of a subject on a game, a response of the subject to a stimulus, a response of the subject to a stimulus on a display visible to the subject, a response of the subject when asked to pop bubbles with his or her fingers, an observation of the subject, a video observation of the subject, or a clinical observation of the subject.

In any apparatus for evaluating a subject as disclosed herein, the apparatus may further comprise a memory having an assessment model stored thereon, the assessment model comprising statistical correlations between a plurality of clinical characteristics and clinical diagnoses of the two or more developmental disorders. The processor may be further configured with instructions to determine whether the subject is at greater risk of the first developmental disorder or the second developmental disorder in response to the assessment model.

In any apparatus for evaluating a subject as disclosed herein, the first developmental disorder and the second developmental disorder may comprise a comorbidity. The first developmental disorder and the second developmental disorder may comprise a comorbidity and the subject may be at greater risk of the first disorder than the second disorder.

In any apparatus for evaluating a subject as disclosed herein, the plurality of questions may comprise a plurality of predetermined questions. A question having high covariance with a question already answered by the subject may not be identified as the most predictive next question.

In any apparatus for evaluating a subject as disclosed herein, the apparatus may further comprise an input and a display coupled to the input. The processor may be configured with instructions to display the plurality of questions and receive the plurality of answers to the plurality of questions via the input, and to display the identified most predictive next question.

In any apparatus for evaluating a subject as disclosed herein, the processor may be configured to determine the subject as at risk of the developmental disorder with one or more of a confidence interval of at least 85% or a sensitivity and specificity of at least 85%. The processor may be configured to determine the subject as at risk of the developmental disorder with one or more of a confidence interval of at least 90% or a sensitivity and specificity of at least 90%. The processor may be configured with instructions to diagnose the subject with one or more of the two or more developmental disorders. The processor may be configured with instructions to determine a risk of the subject for having each of the two or more developmental disorders.

In any apparatus for evaluating a subject as disclosed herein, the processor may be configured with instructions to determine, in a clinical or nonclinical setting, the subject as at risk for the developmental disorders with a confidence of at least 80% (percent). The processor may be configured with instructions to determine, in a clinical or nonclinical setting, the subject as at risk for one or more of the two or more developmental disorders with a sensitivity of at least 80% (percent) and a specificity of at least 80% (percent).

In any apparatus for evaluating a subject as disclosed herein, the two or more developmental disorders may comprise two or more disorders of Diagnostic and Statistical Manual of Mental Disorders (DSM) IV or DSM V. The two or more developmental disorders may comprise one or more of autism spectrum disorder, a level of autism spectrum disorder (ASD), level 1 of ASD, level 2 of ASD, level 3 of ASD, autism ("classical autism"), Asperger's syndrome ("high functioning autism"), pervasive development disorder (PDD "atypical autism"), pervasive developmental disorder not otherwise specified (PDD-NOS), developmental disorders related to autism spectrum disorder, speech and language delay (SLD), obsessive compulsive disorder (OCD), social communication disorder, intellectual disabilities, learning disabilities, sensory processing, attention deficit disorder (ADD), attention deficit hyperactive disorder (ADHD), speech disorder, language disorder, deficits in social communication, deficits in social interaction, restricted repetitive behaviors (RBBs), restrictive repetitive interests, restrictive repetitive activities, global developmental delay, or other behavioral, intellectual, or developmental delay. The two or more developmental disorders may comprise a plurality of disorders having related symptoms, the plurality of disorders having related symptoms of one or more of Autism, Asperger's syndrome, pervasive developmental disorder not otherwise specified (PDD-NOS), ADHD, speech and language delay, OCD, or social communication disorder.

In any apparatus for evaluating a subject as disclosed herein, the processor may comprise one or more of a local processor or a remote server. The processor may comprise one or more of a local processor or a remote server, wherein the processor may be configured to select a next question with sufficient statistics stored on one or more of the local processor or the remote server.

In another aspect, disclosed herein is a method of evaluating a subject for risk of having a developmental disorder among two or more related developmental disorders. The method comprises presenting a question to the subject, the question configured to assess a clinical characteristic related to the two or more related developmental disorders. The method further comprises receiving an answer corresponding to the clinical characteristic of the subject related to the two or more related developmental disorders. The method further comprises determining, in response to the answer, whether the subject is at greater risk of a first developmental disorder or a second developmental disorder of the two or more related developmental disorders with a sensitivity and specificity of at least 80%.

In another aspect, disclosed herein is a method of evaluating a subject for risk of having a developmental disorder among two or more related developmental disorders. The method comprises presenting a question to the subject, the question configured to assess a clinical characteristic related to the two or more related developmental disorders. The method further comprises receiving an answer corresponding to the clinical characteristic of the subject related to the two or more related developmental disorders. The method further comprises determining, in response to the answer, whether the subject is at greater risk of a first developmental disorder or a second developmental disorder of the two or more related developmental disorders, in response to an assessment model comprising statistical correlations between a plurality of clinical characteristics and clinical diagnoses of the two or more related developmental disorders.

In another aspect, disclosed herein is a method of evaluating a subject for risk of having a developmental disorder among two or more related developmental disorders. The method comprises presenting a question to the subject, the question configured to assess a clinical characteristic related to the two or more related developmental disorders. The method further comprises receiving an answer corresponding to the clinical characteristic of the subject related to the two or more related developmental disorders. The method further comprises determining, in response to the answer, whether the subject is at risk of a first developmental disorder and a second developmental disorder of the two or more related developmental disorders with comorbidity, with a sensitivity and specificity of at least 80%.

In another aspect, disclosed herein is a method of evaluating a subject for risk of having a developmental disorder among two or more related developmental disorders. The method comprises receiving a plurality of answers to a plurality of asked questions among a plurality of questions, the plurality of answers corresponding to clinical characteristics of the subject related to the two or more related developmental disorders. A plurality of remaining unasked questions of the plurality of questions comprises a most predictive next question. The method further comprises determining, based on the plurality of answers, whether the subject is at greater risk of a first developmental disorder or a second developmental disorder of the two or more developmental disorders. The method further comprises identifying the most predictive next question among the plurality of remaining unasked questions, in response a determination of the subject as at greater risk of a first developmental disorder or a second developmental disorder of the two or more related developmental disorders.

A question that is most predictive of the first developmental disorder may be identified as the most predictive next question in response to a determination of the subject as at greater risk of the first developmental disorder. A question that is most predictive of the second developmental disorder may be identified as the most predictive next question in response to a determination of the subject as at greater risk of the second developmental disorder.

The identifying may comprise identifying the most predictive next question in response to the plurality of answers corresponding to the plurality of clinical characteristics of the subject. The plurality of answers may comprise a sequence of answers to a sequence of most predictive next questions.

The identifying may comprise identifying the most predictive next question in response to an estimated predictive utility of each remaining question of the plurality of remaining unasked questions. The estimated predictive utility of each remaining question is determined in response to a combination of a predictive utility of each possible answer to each remaining question and a probability of said each possible answer. The estimated predictive utility of each remaining question may be determined with a summation of products comprising the predictive utility of each possible answer to each remaining question combined with the probability of said each possible answer. The predictive utility of each possible answer may be multiplied by a probability of occurrence for said each possible answer. The predictive utility of each possible answer may correspond to a correlation of said each possible answer with clinical diagnosis of the first developmental disorder. The probability of said each possible answer may be determined in response to one or more answers of the subject corresponding to one or more clinical characteristics of the subject.

The identifying may comprise identifying with sufficient statistics the most predictive next question that is most predictive of the first development disorder. The sufficient statistics may comprise sufficient statistics determined with one or more of a binary tree, a random forest, a decision tree, a plurality of decision trees, a plurality of decision trees with controlled variance, a multinomial logistic regression, a naive Bayes classifier, a linear classifier, an ensemble of linear classifiers, a boosting algorithm, a boosting algorithm trained with stochastic gradient descent, a boosting algorithm comprising training data weighting, a boosting algorithm comprising updating training data weighting, or a boosting algorithm comprising updating misclassified training data with higher weights. The sufficient statistics may comprise sufficient statistics of a classifier trained and validated on one or more subject populations.

The identifying may comprise identifying the most predictive next question in response to a plurality of answers corresponding to a plurality of clinical characteristics of the subject, a plurality of remaining questions, and an informativeness of each question of the plurality of remaining questions determined with the sufficient statistics. The most predictive next question may be identified in response to one or more of an informativeness or an estimated predictive utility of the most predictive next question determined in response to a plurality of answers corresponding to a plurality of clinical characteristics of the subject. The method may further comprise determining an informativeness of the most predictive next question in response to an output of a probabilistic graphical model comprising estimates of probability coefficients determined with logistic regression.

The identifying may comprise identifying the most predictive next question that is most predictive of greater risk of the first developmental disorder using sufficient statistics of a machine learning algorithm configured in response to a plurality of clinically assessed subject populations. The identifying may comprise identifying the most predictive next question in response to an estimated predictive utility of the most predictive next question with respect to each of the two or more developmental disorders. The identifying may comprise identifying the next most predictive question with one or more of a binary tree, a random forest, a decision tree, a plurality of decision trees, a plurality of decision trees with controlled variance, a multinomial logistic regression, a naive Bayes classifier, a linear classifier, or an ensemble of linear classifiers.

The plurality of questions may comprise a plurality of predetermined questions. A question having high covariance with a question already answered by the subject may not be identified as the most predictive next question.

The method may further comprise displaying the plurality of questions on a display, receiving the plurality of answers to the plurality of questions via an input coupled to the display, and displaying the identified most predictive next question on the display.

The identifying may comprise identifying first a first plurality of next most predictive questions of a first disorder, and identifying second a second plurality of next most predictive questions of a second disorder in response to a first plurality of answers to the first plurality of next most predictive questions related to the first disorder. The identifying may comprise identifying each of the plurality of next most predictive questions in response to an answer to an immediately preceding next most predictive question. The identifying may comprise identifying a first plurality of next most predictive questions together and to receive answers to the first plurality of next most predictive questions, and identifying a second plurality of next most predictive questions together in response to the answers to the first plurality of next most predictive questions.

The identifying may comprise identifying a first plurality of next most predictive questions of a first disorder and a second plurality of next most predictive questions of a second disorder. The second plurality of next most predictive questions of the second disorder may be identified in response to answers to the first plurality of next most predictive questions. A next most predictive question of the second plurality of next most predictive questions of the second disorder may be identified in response to first answers to the first plurality of next most predictive questions and second answers to the second plurality of next most predictive questions. The method may further comprise determining a first feature importance related to the first disorder for each of the first plurality of next most predictive questions and a second feature importance related to the second disorder for each of the second plurality of next most predictive questions.

In any method of evaluating a subject as disclosed herein, the determining may comprise determining in response to an assessment model comprising statistical correlations between a plurality of clinical characteristics and clinical diagnoses of the two or more developmental disorders. The determining comprises determining whether the subject is at greater risk of the first developmental disorder or the second developmental disorder in response to the assessment model. The determining may comprise determining whether the subject is at risk of the first developmental disorder and the second developmental disorder with comorbidity. The determining may comprise determining whether the subject is at risk of the first developmental disorder and the second developmental disorder with comorbidity and the subject is at greater risk of the first disorder than the second disorder.

In any method of evaluating a subject as disclosed herein, the determining may comprise determining the subject as at risk of the developmental disorder with one or more of a confidence interval of at least 85% or a sensitivity and specificity of at least 85%. The processor may be configured to determine the subject as at risk of the developmental disorder with one or more of a confidence interval of at least 90% or a sensitivity and specificity of at least 90%.

In any method of evaluating a subject as disclosed herein, the method may further comprise diagnosing the subject with one or more of the two or more related developmental disorders. The method may further comprise determining a risk of the subject for having each of the two or more developmental disorders.

In any method of evaluating a subject as disclosed herein, the determining may comprise determining, in a clinical or nonclinical setting, the subject as at risk for the developmental disorders with a confidence of at least 80% (percent). The determining may comprise determining, in a clinical or nonclinical setting, the subject as at risk for one or more of the two or more developmental disorders with a sensitivity of at least 80% (percent) and a specificity of at least 80% (percent).

In any method of evaluating a subject as disclosed herein, the two or more related developmental disorders may comprise two or more disorders of Diagnostic and Statistical Manual of Mental Disorders (DSM) IV or DSM V. The two or more related developmental disorders may comprise one or more of autism spectrum disorder, a level of autism spectrum disorder (ASD), level 1 of ASD, level 2 of ASD, level 3 of ASD, autism ("classical autism"), Asperger's syndrome ("high functioning autism"), pervasive developmental disorder (PDD "atypical autism"), pervasive developmental disorder not otherwise specified (PDD-NOS), developmental disorders related to autism spectrum disorder, speech and language delay (SLD), obsessive compulsive disorder (OCD), social communication disorder, intellectual disabilities, learning disabilities, sensory processing, attention deficit disorder (ADD), attention deficit hyperactive disorder (ADHD), speech disorder, language disorder, deficits in social communication, deficits in social interaction, restricted repetitive behaviors (RBBs), restrictive repetitive interests, restrictive repetitive activities, global developmental delay, or other behavioral, intellectual, or developmental delay. The two or more related developmental disorders may comprise a plurality of disorders having related symptoms, the plurality of disorders having related symptoms of one or more of Autism, Asperger's syndrome, pervasive developmental disorder not otherwise specified (PDD-NOS), ADHD, speech and language delay, OCD, or social communication disorder.

In any method of evaluating a subject as disclosed herein, the method may further comprise selecting a next question with sufficient statistics stored on one or more of a local processor or a remote server. The method may further comprise displaying the plurality of questions and the most predictive next questions.

In any method of evaluating a subject as disclosed herein, the method may further comprise determining a next most predictive question of a first disorder and a second disorder.

In any method of evaluating a subject as disclosed herein, a field to an unanswered question may be provided with a value.

In another aspect, disclosed herein is a method for providing an apparatus for evaluating risk of a subject as disclosed herein.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1A:
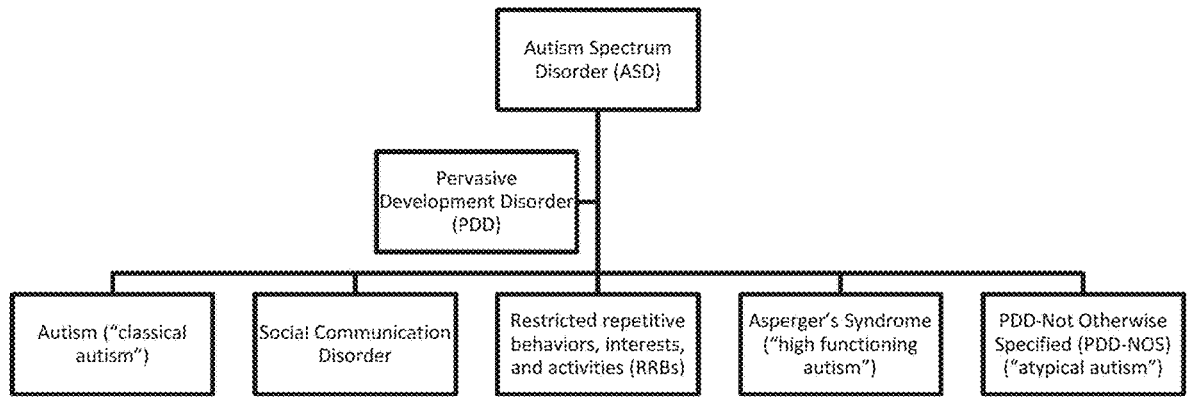
FIGS. 1A and 1B show some exemplary developmental disorders that may be evaluated using the assessment procedure as described herein.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed. It shall be understood that different aspects of the invention can be appreciated individually, collectively, or in combination with each other.

The terms "based on" and "in response to" are used interchangeably with the present disclosure.

The term "processor" encompasses one or more of a local processor, a remote processor, or a processor system, and combinations thereof.

The term "feature" is used herein to describe a characteristic or attribute that is relevant to determining the developmental progress of a subject. For example, a "feature" may refer to a clinical characteristic that is relevant to clinical evaluation or diagnosis of a subject for one or more developmental disorders (e.g., age, ability of subject to engage in pretend play, etc.). The term "feature value" is herein used to describe a particular subject's value for the corresponding feature. For example, a "feature value" may refer to a clinical characteristic of a subject that is related to one or more developmental disorders (e.g., if feature is "age", feature value could be 3; if feature is "ability of subject to engage in pretend play", feature value could be "variety of pretend play" or "no pretend play").

Described herein are methods and apparatus for determining the developmental progress of a subject. For example, the described methods and apparatus can identify a subject as developmentally advanced in one or more areas of development or cognitively declining in one or more cognitive functions, or identify a subject as developmentally delayed or at risk of having one or more developmental disorders. The methods and apparatus disclosed can determine the subject's developmental progress by analyzing a plurality of characteristics or features of the subject based on an assessment model, wherein the assessment model can be generated from large datasets of relevant subject populations using machine-learning approaches.

While methods and apparatus are herein described in the context of identifying one or more developmental disorders of a subject, the methods and apparatus are well-suited for use in determining any developmental progress of a subject. For example, the methods and apparatus can be used to identify a subject as developmentally advanced, by identifying one or more areas of development in which the subject is advanced. To identify one or more areas of advanced development, the methods and apparatus may be configured to assess one or more features or characteristics of the subject that are related to advanced or gifted behaviors, for example. The methods and apparatus as described can also be used to identify a subject as cognitively declining in one or more cognitive functions, by evaluating the one or more cognitive functions of the subject.

Described herein are methods and apparatus for diagnosing or assessing risk for one or more developmental disorders in a subject. The method may comprise providing a data processing module, which can be utilized to construct and administer an assessment procedure for screening a subject for one or more of a plurality of developmental disorders or conditions. The assessment procedure can evaluate a plurality of features or characteristics of the subject, wherein each feature can be related to the likelihood of the subject having at least one of the plurality of developmental disorders screenable by the procedure. Each feature may be related to the likelihood of the subject having two or more related developmental disorders, wherein the two or more related disorders may have one or more related symptoms. The features can be assessed in many ways. For example, the features may be assessed via a subject's answers to questions, observations of a subject, or results of a structured interaction with a subject, as described in further detail herein.

To distinguish among a plurality of developmental disorders of the subject within a single screening procedure, the procedure can dynamically select the features to be evaluated in the subject during administration of the procedure, based on the subject's values for previously presented features (e.g., answers to previous questions). The assessment procedure can be administered to a subject or a caretaker of the subject with a user interface provided by a computing device. The computing device comprises a processor having instructions stored thereon to allow the user to interact with the data processing module through a user interface. The assessment procedure may take less than 10 minutes to administer to the subject, for example 5 minutes or less. Thus, apparatus and methods described herein can provide a prediction of a subject's risk of having one or more of a plurality of developmental disorders using a single, relatively short screening procedure.

The methods and apparatus disclosed herein can be used to determine a most relevant next question related to a feature of a subject, based on previously identified features of the subject. For example, the methods and apparatus can be configured to determine a most relevant next question in response to previously answered questions related to the subject. A most predictive next question can be identified after each prior question is answered, and a sequence of most predictive next questions and a corresponding sequence of answers generated. The sequence of answers may comprise an answer profile of the subject, and the most predictive next question can be generated in response to the answer profile of the subject.

The methods and apparatus disclosed herein are well suited for combinations with prior questions that can be used to diagnose or identify the subject as at risk in response to fewer questions by identifying the most predictive next question in response to the previous answers, for example.

Figure 1B:
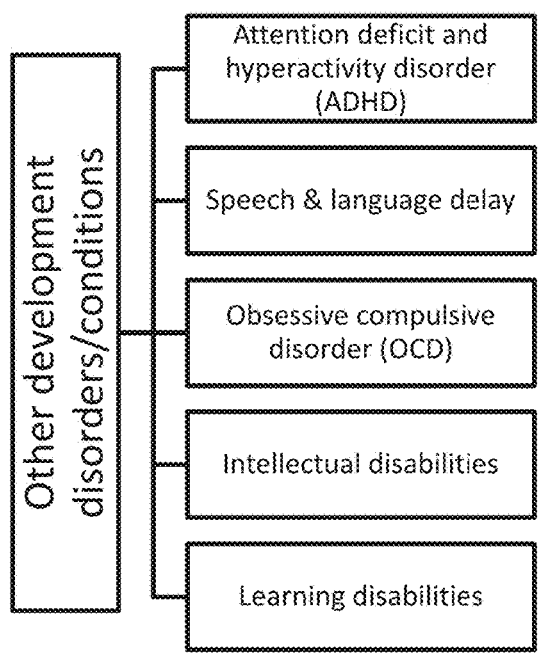

FIGS. 1A and 1B show some exemplary developmental disorders that may be evaluated using the assessment procedure as described herein. The assessment procedure can be configured to evaluate a subject's risk for having one or more developmental disorders, such as two or more related developmental disorders. The developmental disorders may have at least some overlap in symptoms or features of the subject. Such developmental disorders may include pervasive development disorder (PDD), autism spectrum disorder (ASD), social communication disorder, restricted repetitive behaviors, interests, and activities (RRBs), autism ("classical autism"), Asperger's Syndrome ("high functioning autism), PDD-not otherwise specified (PDD-NOS, "atypical autism"), attention deficit and hyperactivity disorder (ADHD), speech and language delay, obsessive compulsive disorder (OCD), intellectual disability, learning disability, or any other relevant development disorder, such as disorders defined in any edition of the Diagnostic and Statistical Manual of Mental Disorders (DSM). The assessment procedure may be configured to determine the risk of the subject for having each of a plurality of disorders. The assessment procedure may be configured to determine the subject as at greater risk of a first disorder or a second disorder of the plurality of disorders. The assessment procedure may be configured to determine the subject as at risk of a first disorder and a second disorder with comorbidity. The assessment procedure may be configured to predict a subject to have normal development, or have low risk of having any of the disorders the procedure is configured to screen for. The assessment procedure may further be configured to have high sensitivity and specificity to distinguish among different severity ratings for a disorder; for example, the procedure may be configured to predict a subject's risk for having level 1 ASD, level 2 ASD, or level 3 ASD as defined in the fifth edition of the DSM (DSM-V).

Many developmental disorders may have similar or overlapping symptoms, thus complicating the assessment of a subject's developmental disorder. The assessment procedure described herein can be configured to evaluate a plurality of features of the subject that may be relevant to one or more developmental disorders. The procedure can comprise an assessment model that has been trained using a large set of clinically validated data to learn the statistical relationship between a feature of a subject and clinical diagnosis of one or more developmental disorders. Thus, as a subject participates in the assessment procedure, the subject's feature value for each evaluated feature (e.g., subject's answer to a question) can be queried against the assessment model to identify the statistical correlation, if any, of the subject's feature value to one or more screened developmental disorders. Based on the feature values provided by the subject, and the relationship between those values and the predicted risk for one or more developmental disorders as determined by the assessment model, the assessment procedure can dynamically adjust the selection of next features to be evaluated in the subject. The selection of the next feature to be evaluated may comprise an identification of the next most predictive feature, based on the determination of the subject as at risk for a particular disorder of the plurality of disorders being screened. For example, if after the subject has answered the first five questions of the assessment procedure, the assessment model predicts a low risk of autism and a relatively higher risk of ADHD in the subject, the assessment procedure may select features with higher relevance to ADHD to be evaluated next in the subject (e.g., questions whose answers are highly correlated with a clinical diagnosis of ADHD may be presented next to the subject). Thus, the assessment procedure described herein can be dynamically tailored to a particular subject's risk profile, and enable the evaluation of the subject's disorder with a high level of granularity.

Figure 2:
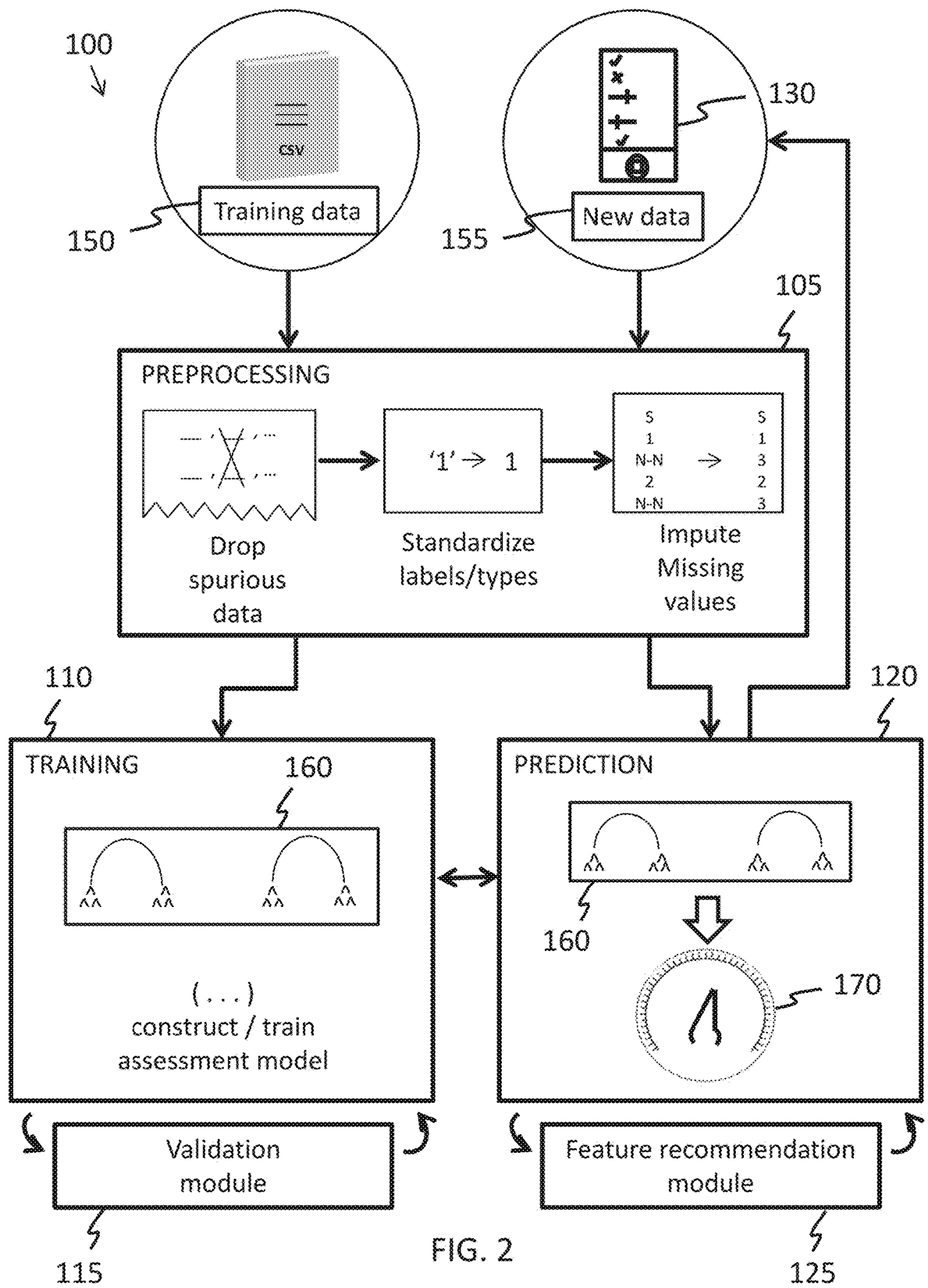
FIG. 2 is a schematic diagram of an exemplary data processing module for providing the assessment procedure as described herein.

FIG. 2 is a schematic diagram of an exemplary data processing module 100 for providing the assessment procedure as described herein. The data processing module 100 generally comprises a preprocessing module 105, a training module 110, and a prediction module 120. The data processing module can extract training data 150 from a database, or intake new data 155 with a user interface 130. The preprocessing module can apply one or more transformations to standardize the training data or new data for the training module or the prediction module. The preprocessed training data can be passed to the training module, which can construct an assessment model 160 based on the training data. The training module may further comprise a validation module 115, configured to validate the trained assessment model using any appropriate validation algorithm (e.g., Stratified K-fold cross-validation). The preprocessed new data can be passed on to the prediction module, which may output a prediction 170 of the subject's developmental disorder by fitting the new data to the assessment model constructed in the training module. The prediction module may further comprise a feature recommendation module 125, configured to select or recommend the next feature to be evaluated in the subject, based on previously provided feature values for the subject.

The training data 150, used by the training module to construct the assessment model, can comprise a plurality of datasets from a plurality of subjects, each subject's dataset comprising an array of features and corresponding feature values, and a classification of the subject's developmental disorder or condition. As described herein, the features may be evaluated in the subject via one or more of questions asked to the subject, observations of the subject, or structured interactions with the subject. Feature values may comprise one or more of answers to the questions, observations of the subject such as characterizations based on video images, or responses of the subject to a structured interaction, for example. Each feature may be relevant to the identification of one or more developmental disorders or conditions, and each corresponding feature value may indicate the degree of presence of the feature in the specific subject. For example, a feature may be the ability of the subject to engage in imaginative or pretend play, and the feature value for a particular subject may be a score of either 0, 1, 2, 3, or 8, wherein each score corresponds to the degree of presence of the feature in the subject (e.g., 0=variety of pretend play; 1=some pretend play; 2=occasional pretending or highly repetitive pretend play; 3=no pretend play; 8=not applicable). The feature may be evaluated in the subject by way of a question presented to the subject or a caretaker such as a parent, wherein the answer to the question comprises the feature value. Alternatively or in combination, the feature may be observed in the subject, for example with a video of the subject engaging in a certain behavior, and the feature value may be identified through the observation. In addition to the array of features and corresponding feature values, each subject's dataset in the training data also comprises a classification of the subject. For example, the classification may be autism, autism spectrum disorder (ASD), or non-spectrum. Preferably, the classification comprises a clinical diagnosis, assigned by qualified personnel such as licensed clinical psychologists, in order to improve the predictive accuracy of the generated assessment model. The training data may comprise datasets available from large data repositories, such as Autism Diagnostic Interview-Revised (ADI-R) data and/or Autism Diagnostic Observation Schedule (ADOS) data available from the Autism Genetic Resource Exchange (AGRE), or any datasets available from any other suitable repository of data (e.g., Boston Autism Consortium (AC), Simons Foundation, National Database for Autism Research, etc.). Alternatively or in combination, the training data may comprise large self-reported datasets, which can be crowd-sourced from users (e.g., via websites, mobile applications, etc.).

The preprocessing module 105 can be configured to apply one or more transformations to the extracted training data to clean and normalize the data, for example. The preprocessing module can be configured to discard features which contain spurious metadata or contain very few observations. The preprocessing module can be further configured to standardize the encoding of feature values. Different datasets may often have the same feature value encoded in different ways, depending on the source of the dataset. For example, '900', '900.0', '904', '904.0', '−1', '−1.0', 'None', and 'NaN' may all encode for a "missing" feature value. The preprocessing module can be configured to recognize the encoding variants for the same feature value, and standardize the datasets to have a uniform encoding for a given feature value. The preprocessing module can thus reduce irregularities in the input data for the training and prediction modules, thereby improving the robustness of the training and prediction modules.

In addition to standardizing data, the preprocessing module can also be configured to re-encode certain feature values into a different data representation. In some instances, the original data representation of the feature values in a dataset may not be ideal for the construction of an assessment model. For example, for a categorical feature wherein the corresponding feature values are encoded as integers from 1 to 9, each integer value may have a different semantic content that is independent of the other values. For example, a value of '1' and a value of '9' may both be highly correlated with a specific classification, while a value of '5' is not. The original data representation of the feature value, wherein the feature value is encoded as the integer itself, may not be able to capture the unique semantic content of each value, since the values are represented in a linear model (e.g., an answer of '5' would place the subject squarely between a '1' and a '9' when the feature is considered in isolation; however, such an interpretation would be incorrect in the aforementioned case wherein a '1' and a '9' are highly correlated with a given classification while a '5' is not). To ensure that the semantic content of each feature value is captured in the construction of the assessment model, the preprocessing module may comprise instructions to re-encode certain feature values, such as feature values corresponding to categorical features, in a "one-hot" fashion, for example. In a "one-hot" representation, a feature value may be represented as an array of bits having a value of 0 or 1, the number of bits corresponding to the number of possible values for the feature. Only the feature value for the subject may be represented as a "1", with all other values represented as a "0". For example, if a subject answered "4" to a question whose possible answers comprise integers from 1 to 9, the original data representation may be [4], and the one-hot representation may be [0 0 0 1 0 0 0 0 0]. Such a one-hot representation of feature values can allow every value to be considered independently of the other possible values, in cases where such a representation would be necessary. By thus re-encoding the training data using the most appropriate data representation for each feature, the preprocessing module can improve the accuracy of the assessment model constructed using the training data.

The preprocessing module can be further configured to impute any missing data values, such that downstream modules can correctly process the data. For example, if a training dataset provided to the training module comprises data missing an answer to one of the questions, the preprocessing module can provide the missing value, so that the dataset can be processed correctly by the training module. Similarly, if a new dataset provided to the prediction module is missing one or more feature values (e.g., the dataset being queried comprises only the answer to the first question in a series of questions to be asked), the preprocessing module can provide the missing values, so as to enable correct processing of the dataset by the prediction module. For features having categorical feature values (e.g., extent of display of a certain behavior in the subject), missing values can be provided as appropriate data representations specifically designated as such. For example, if the categorical features are encoded in a one-hot representation as described herein, the preprocessing module may encode a missing categorical feature value as an array of '0' bits. For features having continuous feature values (e.g., age of the subject), the mean of all of the possible values can be provided in place of the missing value (e.g., age of 4 years).

The training module 110 can utilize a machine learning algorithm or other algorithm to construct and train an assessment model to be used in the assessment procedure, for example. An assessment model can be constructed to capture, based on the training data, the statistical relationship, if any, between a given feature value and a specific developmental disorder to be screened by the assessment procedure. The assessment model may, for example, comprise the statistical correlations between a plurality of clinical characteristics and clinical diagnoses of one or more developmental disorders. A given feature value may have a different predictive utility for classifying each of the plurality of developmental disorders to be evaluated in the assessment procedure. For example, in the aforementioned example of a feature comprising the ability of the subject to engage in imaginative or pretend play, the feature value of "3" or "no variety of pretend play" may have a high predictive utility for classifying autism, while the same feature value may have low predictive utility for classifying ADHD. Accordingly, for each feature value, a probability distribution may be extracted that describes the probability of the specific feature value for predicting each of the plurality of developmental disorders to be screened by the assessment procedure. The machine learning algorithm can be used to extract these statistical relationships from the training data and build an assessment model that can yield an accurate prediction of a developmental disorder when a dataset comprising one or more feature values is fitted to the model.

One or more machine learning algorithms may be used to construct the assessment model, such as support vector machines that deploy stepwise backwards feature selection and/or graphical models, both of which can have advantages of inferring interactions between features. For example, machine learning algorithms or other statistical algorithms may be used, such as alternating decision trees (ADTree), Decision Stumps, functional trees (FT), logistic model trees (LMT), logistic regression, Random Forests, linear classifiers, or any machine learning algorithm or statistical algorithm known in the art. One or more algorithms may be used together to generate an ensemble method, wherein the ensemble method may be optimized using a machine learning ensemble meta-algorithm such as a boosting (e.g., AdaBoost, LPBoost, TotalBoost, BrownBoost, MadaBoost, LogitBoost, etc.) to reduce bias and/or variance. Once an assessment model is derived from the training data, the model may be used as a prediction tool to assess the risk of a subject for having one or more developmental disorders. Machine learning analyses may be performed using one or more of many programming languages and platforms known in the art, such as R, Weka, Python, and/or Matlab, for example.

A Random Forest classifier, which generally comprises a plurality of decision trees wherein the output prediction is the mode of the predicted classifications of the individual trees, can be helpful in reducing overfitting to training data. An ensemble of decision trees can be constructed using a random subset of features at each split or decision node. The Gini criterion may be employed to choose the best partition, wherein decision nodes having the lowest calculated Gini impurity index are selected. At prediction time, a "vote" can be taken over all of the decision trees, and the majority vote (or mode of the predicted classifications) can be output as the predicted classification.

Figure 3:
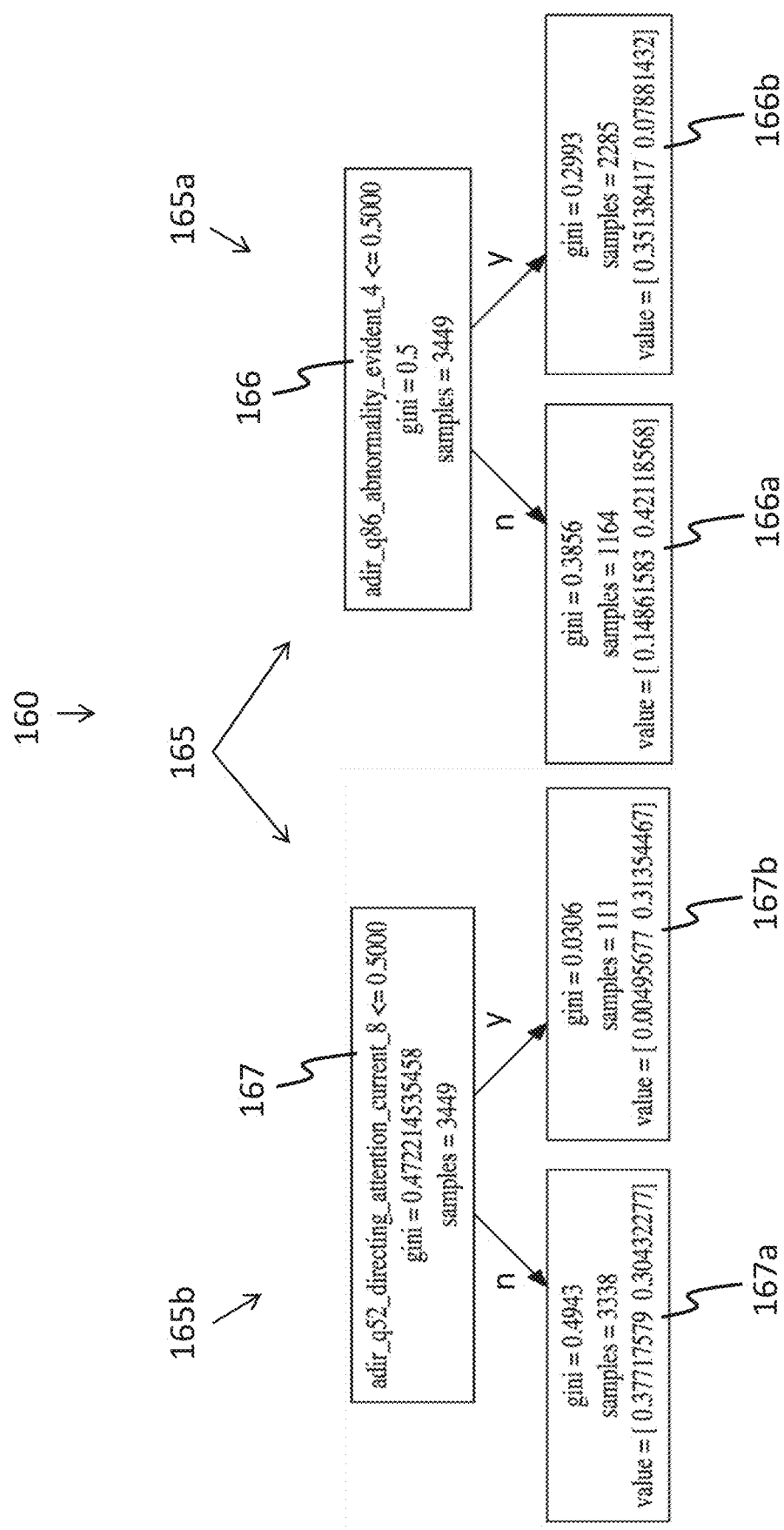
FIG. 3 is a schematic diagram illustrating a portion of an exemplary assessment model based on a Random Forest classifier.

FIG. 3 is a schematic diagram illustrating a portion of an exemplary assessment model 160 based on a Random Forest classifier. The assessment module may comprise a plurality of individual decision trees 165, such as decision trees 165a and 165b, each of which can be generated independently using a random subset of features in the training data. Each decision tree may comprise one or more decision nodes such as decision nodes 166 and 167 shown in FIG. 3, wherein each decision node specifies a predicate condition. For example, decision node 16 predicates the condition that, for a given dataset of an individual, the answer to ADI-R question #86 (age when abnormality is first evident) is 4 or less. Decision node 167 predicates the condition that, for the given dataset, the answer to ADI-R question #52 (showing and direction attention) is 8 or less. At each decision node, a decision tree can be split based on whether the predicate condition attached to the decision node holds true, leading to prediction nodes (e.g., 166a, 166b, 167a, 167b). Each prediction node can comprise output values ('value' in FIG. 3) that represent "votes" for one or more of the classifications or conditions being evaluated by the assessment model. For example, in the prediction nodes shown in FIG. 3, the output values comprise votes for the individual being classified as having autism or being non-spectrum. A prediction node can lead to one or more additional decision nodes downstream (not shown in FIG. 3), each decision node leading to an additional split in the decision tree associated with corresponding prediction nodes having corresponding output values. The Gini impurity can be used as a criterion to find informative features based on which the splits in each decision tree may be constructed.

When the dataset being queried in the assessment model reaches a "leaf", or a final prediction node with no further downstream splits, the output values of the leaf can be output as the votes for the particular decision tree. Since the Random Forest model comprises a plurality of decision trees, the final votes across all trees in the forest can be summed to yield the final votes and the corresponding classification of the subject. While only two decision trees are shown in FIG. 3, the model can comprise any number of decision trees. A large number of decision trees can help reduce overfitting of the assessment model to the training data, by reducing the variance of each individual decision tree. For example, the assessment model can comprise at least about 10 decision trees, for example at least about 100 individual decision trees or more.

An ensemble of linear classifiers may also be suitable for the derivation of an assessment model as described herein. Each linear classifier can be individually trained with a stochastic gradient descent, without an "intercept term". The lack of an intercept term can prevent the classifier from deriving any significance from missing feature values. For example, if a subject did not answer a question such that the feature value corresponding to said question is represented as an array of '0' bits in the subject's data set, the linear classifier trained without an intercept term will not attribute any significance to the array of '0' bits. The resultant assessment model can thereby avoid establishing a correlation between the selection of features or questions that have been answered by the subject and the final classification of the subject as determined by the model. Such an algorithm can help ensure that only the subject-provided feature values or answers, rather than the features or questions, are factored into the final classification of the subject.

The training module may comprise feature selection. One or more feature selection algorithms (such as support vector machine, convolutional neural nets) may be used to select features able to differentiate between individuals with and without certain developmental disorders. Different sets of features may be selected as relevant for the identification of different disorders. Stepwise backwards algorithms may be used along with other algorithms. The feature selection procedure may include a determination of an optimal number of features.

The training module may be configured to evaluate the performance of the derived assessment models. For example, the accuracy, sensitivity, and specificity of the model in classifying data can be evaluated. The evaluation can be used as a guideline in selecting suitable machine learning algorithms or parameters thereof. The training module can thus update and/or refine the derived assessment model to maximize the specificity (the true negative rate) over sensitivity (the true positive rate). Such optimization may be particularly helpful when class imbalance or sample bias exists in training data.

In at least some instances, available training data may be skewed towards individuals diagnosed with a specific developmental disorder. In such instances, the training data may produce an assessment model reflecting that sample bias, such that the model assumes that subjects are at risk for the specific developmental disorder unless there is a strong case to be made otherwise. An assessment model incorporating such a particular sample bias can have less than ideal performance in generating predictions of new or unclassified data, since the new data may be drawn from a subject population which may not comprise a sample bias similar to that present in the training data. To reduce sample bias in constructing an assessment model using skewed training data, sample weighting may be applied in training the assessment model. Sample weighting can comprise lending a relatively greater degree of significance to a specific set of samples during the model training process. For example, during model training, if the training data is skewed towards individuals diagnosed with autism, higher significance can be attributed to the data from individuals not diagnosed with autism (e.g., up to 50 times more significance than data from individuals diagnosed with autism). Such a sample weighting technique can substantially balance the sample bias present in the training data, thereby producing an assessment model with reduced bias and improved accuracy in classifying data in the real world. To further reduce the contribution of training data sample bias to the generation of an assessment model, a boosting technique may be implemented during the training process. Boosting comprises an iterative process, wherein after one iteration of training, the weighting of each sample data point is updated. For example, samples that are misclassified after the iteration can be updated with higher significances. The training process may then be repeated with the updated weightings for the training data.

The training module may further comprise a validation module 115 configured to validate the assessment model constructed using the training data. For example, a validation module may be configured to implement a Stratified K-fold cross validation, wherein k represents the number of partitions that the training data is split into for cross validation. For example, k can be any integer greater than 1, such as 3, 4, 5, 6, 7, 8, 9, or 10, or possibly higher depending on risk of overfitting the assessment model to the training data.

The training module may be configured to save a trained assessment model to a local memory and/or a remote server, such that the model can be retrieved for modification by the training module or for the generation of a prediction by the prediction module 120.

Figure 4:
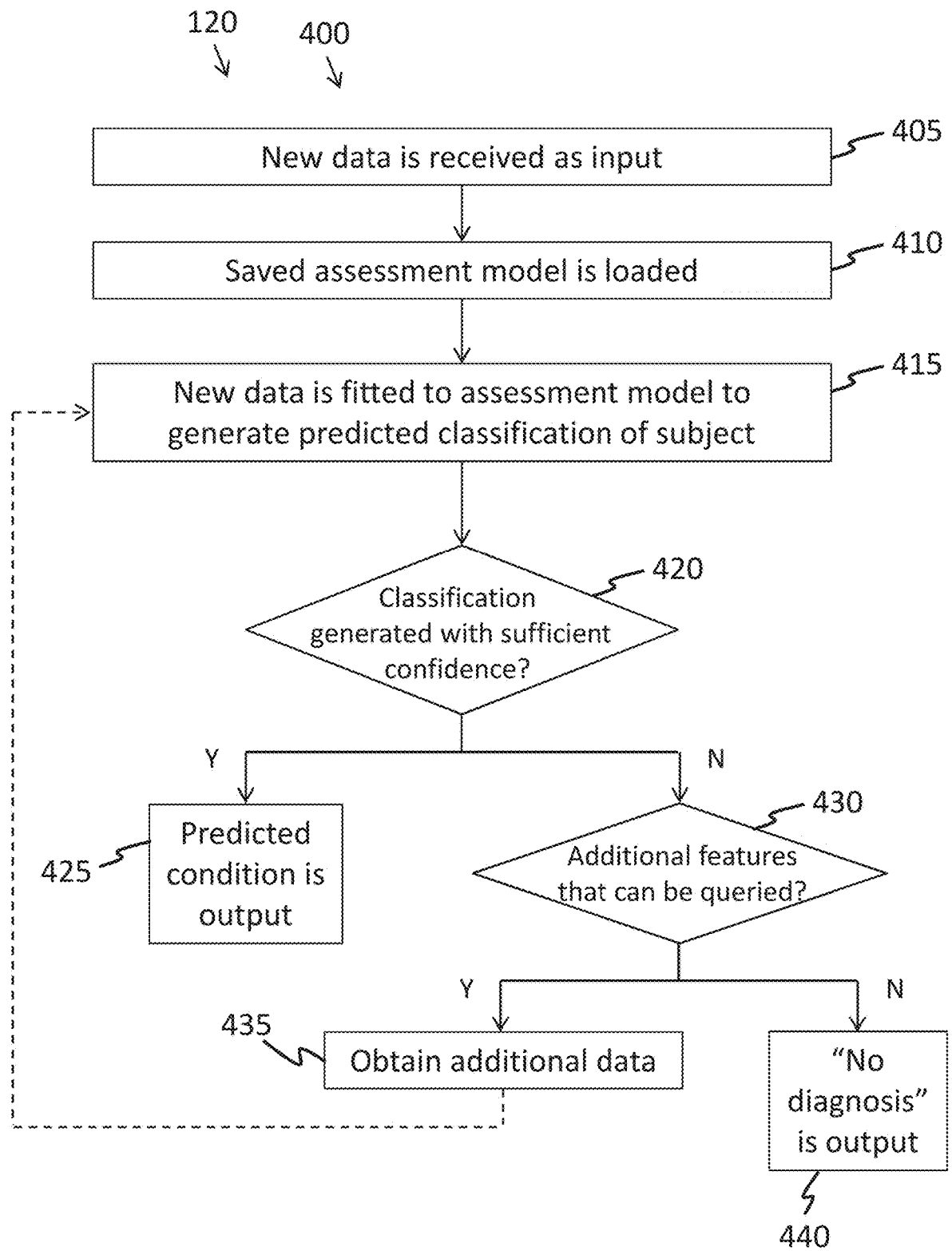
FIG. 4 is an exemplary operational flow of a prediction module as described herein.

FIG. 4 is an exemplary operational flow 400 of a method of a prediction module 120 as described herein. The prediction module 120 can be configured to generate a predicted classification (e.g., developmental disorder) of a given subject, by fitting new data to an assessment model constructed in the training module. At step 405, the prediction module can receive new data that may have been processed by the preprocessing module to standardize the data, for example by dropping spurious metadata, applying uniform encoding of feature values, re-encoding select features using different data representations, and/or imputing missing data points, as described herein. The new data can comprise an array of features and corresponding feature values for a particular subject. As described herein, the features may comprise a plurality of questions presented to a subject, observations of the subject, or tasks assigned to the subject. The feature values may comprise input data from the subject corresponding to characteristics of the subject, such as answers of the subject to questions asked, or responses of the subject. The new data provided to the prediction module may or may not have a known classification or diagnosis associated with the data; either way, the prediction module may not use any pre-assigned classification information in generating the predicted classification for the subject. The new data may comprise a previously-collected, complete dataset for a subject to be diagnosed or assessed for the risk of having one or more of a plurality of developmental disorders. Alternatively or in combination, the new data may comprise data collected in real time from the subject or a caretaker of the subject, for example with a user interface as described in further detail herein, such that the complete dataset can be populated in real time as each new feature value provided by the subject is sequentially queried against the assessment model.

At step 410, the prediction module can load a previously saved assessment model, constructed by the training module, from a local memory and/or a remote server configured to store the model. At step 415, the new data is fitted to the assessment model to generate a predicted classification of the subject. At step 420, the module can check whether the fitting of the data can generate a prediction of one or more specific disorders (e.g., autism, ADHD, etc.) within a confidence interval exceeding a threshold value, for example within a 90% or higher confidence interval, for example 95% or more. If so, as shown in step 425, the prediction module can output the one or more developmental disorders as diagnoses of the subject or as disorders for which the subject is at risk. The prediction module may output a plurality of developmental disorders for which the subject is determined to at risk beyond the set threshold, optionally presenting the plurality of disorders in order of risk. The prediction module may output one developmental disorder for which the subject is determined to be at greatest risk. The prediction module may output two or more development disorders for which the subject is determined to risk with comorbidity. The prediction module may output determined risk for each of the one or more developmental disorders in the assessment model. If the prediction module cannot fit the data to any specific developmental disorder within a confidence interval at or exceeding the designated threshold value, the prediction module may determine, in step 430, whether there are any additional features that can be queried. If the new data comprises a previously-collected, complete dataset, and the subject cannot be queried for any additional feature values, "no diagnosis" may be output as the predicted classification, as shown in step 440. If the new data comprises data collected in real time from the subject or caretaker during the prediction process, such that the dataset is updated with each new input data value provided to the prediction module and each updated dataset is fitted to the assessment model, the prediction module may be able to query the subject for additional feature values. If the prediction module has already obtained data for all features included in the assessment module, the prediction module may output "no diagnosis" as the predicted classification of the subject, as shown in step 440. If there are features that have not yet been presented to the subject, as shown in step 435, the prediction module may obtain additional input data values from the subject, for example by presenting additional questions to the subject. The updated dataset including the additional input data may then be fitted to the assessment model again (step 415), and the loop may continue until the prediction module can generate an output.

Figure 5:
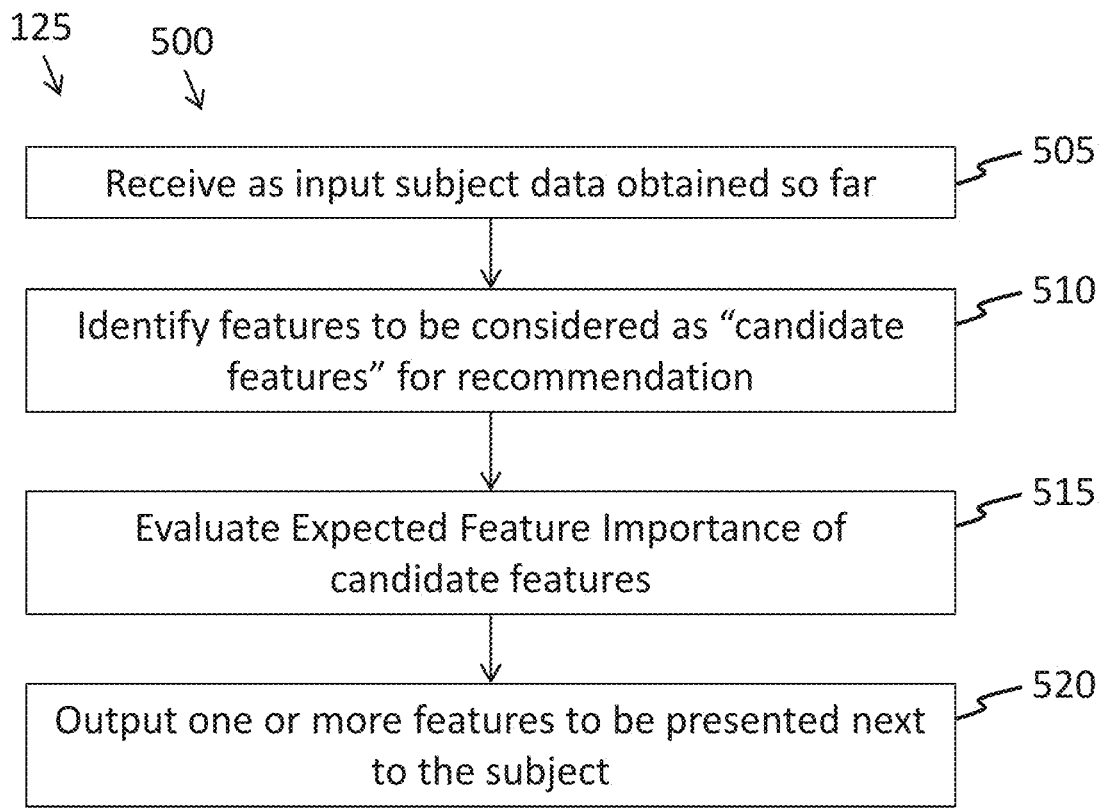
FIG. 5 is an exemplary operational flow of a feature recommendation module as described herein.

FIG. 5 is an exemplary operational flow 500 of a feature recommendation module 125 as described herein by way of a non-limiting example. The prediction module may comprise a feature recommendation module 125, configured to identify, select or recommend the next most predictive or relevant feature to be evaluated in the subject, based on previously provided feature values for the subject. For example, the feature recommendation module can be a question recommendation module, wherein the module can select the most predictive next question to be presented to a subject or caretaker, based on the answers to previously presented questions. The feature recommendation module can be configured to recommend one or more next questions or features having the highest predictive utility in classifying a particular subject's developmental disorder. The feature recommendation module can thus help to dynamically tailor the assessment procedure to the subject, so as to enable the prediction module to produce a prediction with a reduced length of assessment and improved sensitivity and accuracy. Further, the feature recommendation module can help improve the specificity of the final prediction generated by the prediction module, by selecting features to be presented to the subject that are most relevant in predicting one or more specific developmental disorders that the particular subject is most likely to have, based on feature values previously provided by the subject.

At step 505, the feature recommendation module can receive as input the data already obtained from the subject in the assessment procedure. The input subject data can comprise an array of features and corresponding feature values provided by the subject. At step 510, the feature recommendation module can select one or more features to be considered as "candidate features" for recommendation as the next feature(s) to be presented to one or more of the subject, caretaker or clinician. Features that have already been presented can be excluded from the group of candidate features to be considered. Optionally, additional features meeting certain criteria may also be excluded from the group of candidate features, as described in further detail herein.

At step 515, the feature recommendation module can evaluate the "expected feature importance" of each candidate feature. The candidate features can be evaluated for their "expected feature importance", or the estimated utility of each candidate feature in predicting a specific developmental disorder for the specific subject. The feature recommendation module may utilize an algorithm based on: (1) the importance or relevance of a specific feature value in predicting a specific developmental disorder; and (2) the probability that the subject may provide the specific feature value. For example, if the answer of "3" to ADOS question B5 is highly correlated with a classification of autism, this answer can be considered a feature value having high utility for predicting autism. If the subject at hand also has a high probability of answering "3" to said question B5, the feature recommendation module can determine this question to have high expected feature importance. An algorithm that can be used to determine the expected feature importance of a feature is described in further detail in reference to FIG. 6, for example.

At step 520, the feature recommendation module can select one or more candidate features to be presented next to the subject, based on the expected feature importance of the features as determined in step 515. For example, the expected feature importance of each candidate feature may be represented as a score or a real number, which can then be ranked in comparison to other candidate features. The candidate feature having the desired rank, for example a top 10, top 5, top 3, top 2, or the highest rank, may be selected as the feature to the presented next to the subject.

Figure 6:
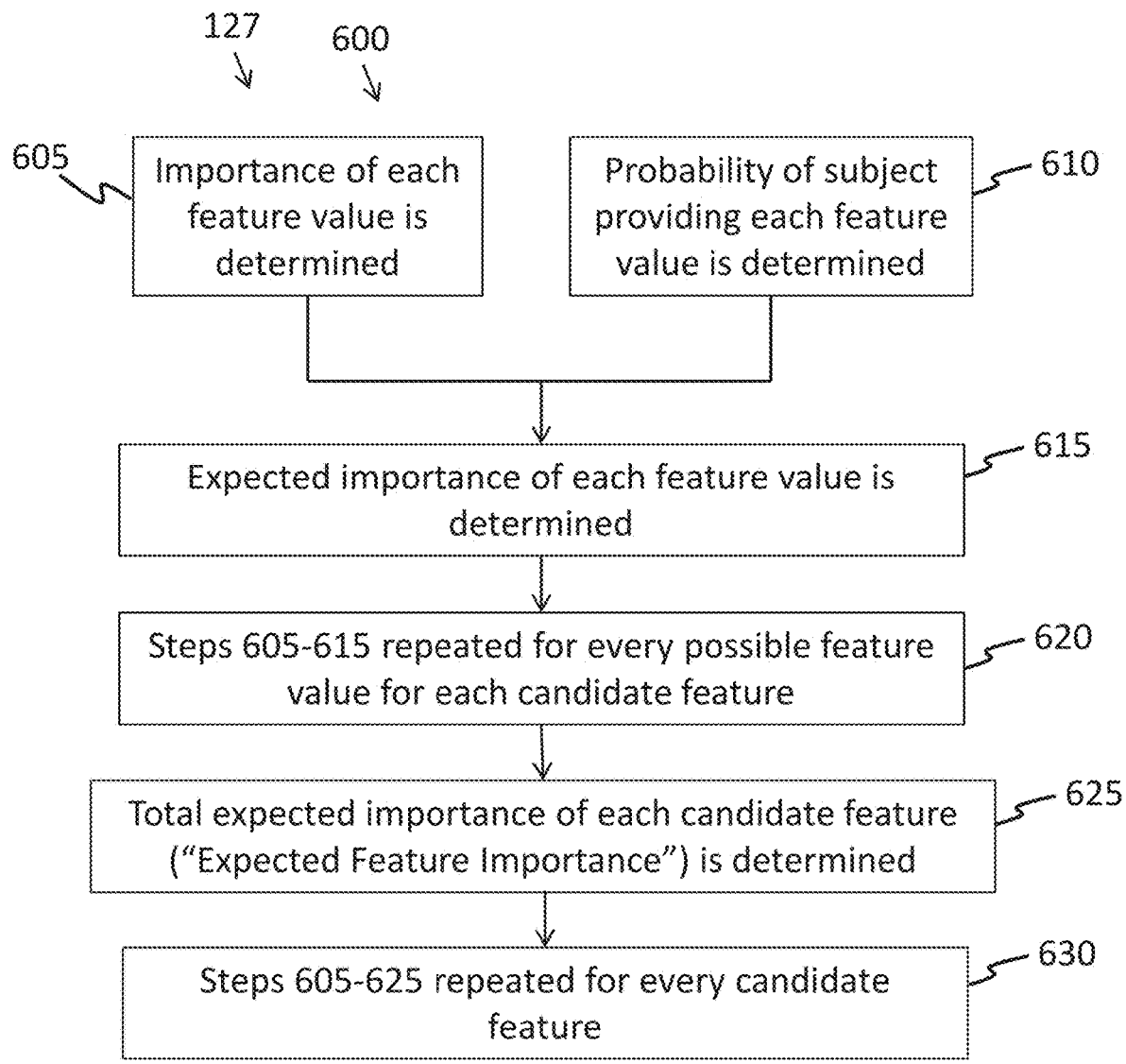
FIG. 6 is an exemplary operational flow of an expected feature importance determination algorithm as performed by a feature recommendation module described herein.

FIG. 6 is an exemplary operational flow 600 of method of determining an expected feature importance determination algorithm 127 as performed by a feature recommendation module 125 described herein.

At step 605, the algorithm can determine the importance or relevance of a specific feature value in predicting a specific developmental disorder. The importance or relevance of a specific feature value in predicting a specific developmental disorder can be derived from the assessment model constructed using training data. Such a "feature value importance" can be conceptualized as a measure of how relevant a given feature value's role is, should it be present or not present, in determining a subject's final classification. For example, if the assessment model comprises a Random Forest classifier, the importance of a specific feature value can be a function of where that feature is positioned in the Random Forest classifier's branches. Generally, if the average position of the feature in the decision trees is relatively high, the feature can have relatively high feature importance. The importance of a feature value given a specific assessment model can be computed efficiently, either by the feature recommendation module or by the training module, wherein the training module may pass the computed statistics to the feature recommendation module. Alternatively, the importance of a specific feature value can be a function of the actual prediction confidence that would result if said feature value was provided by the subject. For each possible feature value for a given candidate feature, the feature recommendation module can be configured to calculate the actual prediction confidence for predicting one or more developmental disorders, based on the subject's previously provided feature values and the currently assumed feature value.

Each feature value may have a different importance for each developmental disorder for which the assessment procedure is designed to screen. Accordingly, the importance of each feature value may be represented as a probability distribution that describes the probability of the feature value yielding an accurate prediction for each of the plurality of developmental disorders being evaluated.

At step 610, the feature recommendation module can determine the probability of a subject providing each feature value. The probability that the subject may provide a specific feature value can be computed using any appropriate statistical model. For example, a large probabilistic graphical model can be used to find the values of expressions such as:

$$\text{prob}(E=1 | A=1, B=2, C=1)$$

where A, B, and C represent different features or questions in the prediction module and the integers 1 and 2 represent different possible feature values for the feature (or possible answers to the questions). The probability of a subject providing a specific feature value may then be computed using Bayes' rule, with expressions such as:

$$\text{prob}(E=1|A=1,B=2,C=1) = \text{prob}(E=1,A=1,B=2,C=1)/\text{prob}(A=1,B=2,C=1)$$

Such expressions may be computationally expensive, in terms of both computation time and required processing resources. Alternatively or in combination with computing the probabilities explicitly using Bayes' rule, logistic regression or other statistical estimators may be used, wherein the probability is estimated using parameters derived from a machine learning algorithm. For example, the following expression may be used to estimate the probability that the subject may provide a specific feature value:

$$\text{prob}(E=1|A=1,B=2,C=1) \approx \text{sigmoid}(a1*A+a2*B+a3*C+a4),$$

wherein a1, a2, a3, and a4 are constant coefficients determined from the trained assessment model, learned using an optimization algorithm that attempts to make this expression maximally correct, and wherein sigmoid is a nonlinear function that enables this expression to be turned into a probability. Such an algorithm can be quick to train, and the resulting expressions can be computed quickly in application, e.g., during administration of the assessment procedure. Although reference is made to four coefficients, as many coefficients as are helpful may be used as will be recognized by a person of ordinary skill in the art.

At step 615, the expected importance of each feature value can be determined based on a combination of the metrics calculated in steps 605 and 610. Based on these two factors, the feature recommendation module can determine the expected utility of the specific feature value in predicting a specific developmental disorder. Although reference is made herein to the determination of expected importance via multiplication, the expected importance can be determined by combining coefficients and parameters in many ways, such as with look up tables, logic, or division, for example.

At step 620, steps 605-615 can be repeated for every possible feature value for each candidate feature. For example, if a particular question has 4 possible answers, the expected importance of each of the 4 possible answers is determined.

At step 625, the total expected importance, or the expected feature importance, of each candidate feature can be determined. The expected feature importance of each feature can be determined by summing the feature value importances of every possible feature value for the feature, as determined in step 620. By thus summing the expected utilities across all possible feature values for a given feature, the feature recommendation module can determine the total expected feature importance of the feature for predicting a specific developmental disorder in response to previous answers.

At step 630, steps 605-625 can be repeated for every candidate feature being considered by the feature recommendation module. The candidate features may comprise a subset of possible features such as questions. Thus, an expected feature importance score for every candidate feature can be generated, and the candidate features can be ranked in order of highest to lowest expected feature importance.

Optionally, in addition to the two factors determined in steps 605 and 610, a third factor may also be taken into account in determining the importance of each feature value. Based on the subject's previously provided feature values, the subject's probability of having one or more of the plurality of developmental disorders can be determined. Such a probability can be determined based on the probability distribution stored in the assessment model, indicating the probability of the subject having each of the plurality of screened developmental disorders based on the feature values provided by the subject. In selecting the next feature to be presented to the subject, the algorithm may be configured to give greater weight to the feature values most important or relevant to predicting the one or more developmental disorders that the subject at hand is most likely to have. For example, if a subject's previously provided feature values indicate that the subject has a higher probability of having either an intellectual disability or speech and language delay than any of the other developmental disorders being evaluated, the feature recommendation module can favor feature values having high importance for predicting either intellectual disability or speech and language delay, rather than features having high importance for predicting autism, ADHD, or any other developmental disorder that the assessment is designed to screen for. The feature recommendation module can thus enable the prediction module to tailor the prediction process to the subject at hand, presenting more features that are relevant to the subject's potential developmental disorder to yield a final classification with higher granularity and confidence.

Although the above steps show an exemplary operational flow 600 of an expected feature importance determination algorithm 127, a person of ordinary skill in the art will recognize many variations based on the teachings described herein. The steps may be completed in a different order. Steps may be added or deleted. Some of the steps may comprise sub-steps of other steps. Many of the steps may be repeated as often as desired by the user.

An exemplary implementation of the feature recommendation module is now described. Subject X has provided answers (feature values) to questions (features) A, B, and C in the assessment procedure:

$$\text{Subject } X = \{`A`:1, `C`:1\}$$

The feature recommendation module can determine whether question D or question E should be presented next in order to maximally increase the predictive confidence with which a final classification or diagnosis can be reached. Given Subject X's previous answers, the feature recommendation module determines the probability of Subject X providing each possible answer to each of questions D and E, as follows:

$$\text{prob}(E=1|A=1,B=2,C=1)=0.1$$

$$\text{prob}(E=2|A=1,B=2,C=1)=0.9$$

$$\text{prob}(D=1|A=1,B=2,C=1)=0.7$$

$$\text{prob}(D=2|A=1,B=2,C=1)=0.3$$

The feature importance of each possible answer to each of questions D and E can be computed based on the assessment model as described. Alternatively, the feature importance of each possible answer to each of questions D and E can be computed as the actual prediction confidence that would result if the subject were to give the specific answer. The importance of each answer can be represented using a range of values on any appropriate numerical scale. For example:

$$\text{importance}(E=1)=1$$

$$\text{importance}(E=2)=3$$

importance($D=1$)=2 importance($D=2$)=4

Based on the computed probabilities and the feature value importances, the feature recommendation module can compute the expected feature importance of each question as follows:

$$\begin{aligned}\text{Expectation [importance}(E)] &= (prob(E=1\mid A=1, B=2,\ C=1) * \\ &\quad \text{importance}(E=1) + \\ &\quad (prob(E=2\mid A=1, B=2,\ C=1) * \\ &\quad \text{importance}(E=2) \\ &= 0.1*1 + 0.9*3 \\ &= 2.8\end{aligned}$$

$$\begin{aligned}\text{Expectation [importance}(D)] &= (prob(D=1\mid A=1, B=2,\ C=1) * \\ &\quad \text{importance}(D=1) + \\ &\quad (prob(D=2\mid A=1, B=2,\ C=1) * \\ &\quad \text{importance}(D=2) \\ &= 0.7*2 + 0.3*4 \\ &= 2.6\end{aligned}$$

Hence, the expected feature importance (also referred to as relevance) from the answer of question E is determined to be higher than that of question D, even though question D has generally higher feature importances for its answers. The feature recommendation module can therefore select question E as the next question to be presented to Subject X.

When selecting the next best feature to be presented to a subject, the feature recommendation module 125 may be further configured to exclude one or more candidate features from consideration, if the candidate features have a high co-variance with a feature that has already been presented to the subject. The co-variance of different features may be determined based on the training data, and may be stored in the assessment model constructed by the training module. If a candidate feature has a high co-variance with a previously presented feature, the candidate feature may add relatively little additional predictive utility, and may hence be omitted from future presentation to the subject in order to optimize the efficiency of the assessment procedure.

The prediction module 120 may interact with the person participating in the assessment procedure (e.g., a subject or the subject's caretaker) with a user interface 130. The user interface may be provided with a user interface, such as a display of any computing device that can enable the user to access the prediction module, such as a personal computer, a tablet, or a smartphone. The computing device may comprise a processor that comprises instructions for providing the user interface, for example in the form of a mobile application. The user interface can be configured to display instructions from the prediction module to the user, and/or receive input from the user with an input method provided by the computing device. Thus, the user can participate in the assessment procedure as described herein by interacting with the prediction module with the user interface, for example by providing answers (feature values) in response to questions (features) presented by the prediction module. The user interface may be configured to administer the assessment procedure in real-time, such that the user answers one question at a time and the prediction module can select the next best question to ask based on recommendations made by the feature recommendation module.

Alternatively or in combination, the user interface may be configured to receive a complete set of new data from a user, for example by allowing a user to upload a complete set of feature values corresponding to a set of features.

As described herein, the features of interest relevant to identifying one or more developmental disorders may be evaluated in a subject in many ways. For example, the subject or caretaker or clinician may be asked a series of questions designed to assess the extent to which the features of interest are present in the subject. The answers provided can then represent the corresponding feature values of the subject. The user interface may be configured to present a series of questions to the subject (or any person participating in the assessment procedure on behalf of the subject), which may be dynamically selected from a set of candidate questions as described herein. Such a question-and-answer based assessment procedure can be administered entirely by a machine, and can hence provide a very quick prediction of the subject's developmental disorder(s).

Alternatively or in combination, features of interest in a subject may be evaluated with observation of the subject's behaviors, for example with videos of the subject. The user interface may be configured to allow a subject or the subject's caretaker to record or upload one or more videos of the subject. The video footage may be subsequently analyzed by qualified personnel to determine the subject's feature values for features of interest. Alternatively or in combination, video analysis for the determination of feature values may be performed by a machine. For example, the video analysis may comprise detecting objects (e.g., subject, subject's spatial position, face, eyes, mouth, hands, limbs, fingers, toes, feet, etc.), followed by tracking the movement of the objects. The video analysis may infer the gender of the subject, and/or the proficiency of spoken language(s) of the subject. The video analysis may identify faces globally, or specific landmarks on the face such as the nose, eyes, lips and mouth to infer facial expressions and track these expressions over time. The video analysis may detect eyes, limbs, fingers, toes, hands, feet, and track their movements over time to infer behaviors. In some cases, the analysis may further infer the intention of the behaviors, for example, a child being upset by noise or loud music, engaging in self-harming behaviors, imitating another person's actions, etc. The sounds and/or voices recorded in the video files may also be analyzed. The analysis may infer a context of the subject's behavior. The sound/voice analysis may infer a feeling of the subject. The analysis of a video of a subject, performed by a human and/or by a machine, can yield feature values for the features of interest, which can then be encoded appropriately for input into the prediction module. A prediction of the subject's developmental disorder may then be generated based on a fitting of the subject's feature values to the assessment model constructed using training data.

Alternatively or in combination, features of interest in a subject may be evaluated through structured interactions with the subject. For example, the subject may be asked to play a game such as a computer game, and the performance of the subject on the game may be used to evaluate one or more features of the subject. The subject may be presented with one or more stimuli (e.g., visual stimuli presented to the subject via a display), and the response of the subject to the stimuli may be used to evaluate the subject's features. The subject may be asked to perform a certain task (e.g., subject may be asked to pop bubbles with his or her fingers), and the response of the subject to the request or the ability of the subject to carry out the requested task may be used to evaluate to the subject's features.

The methods and apparatus described herein can be configured in many ways to determine the next most predictive or relevant question. At least a portion of the software instructions as described herein can be configured to run locally on a local device so as to provide the user interface and present questions and receive answers to the questions. The local device can be configured with software instructions of an application program interface (API) to query a remote server for the most predictive next question. The API can return an identified question based on the feature importance as described herein, for example. Alternatively or in combination, the local processor can be configured with instructions to determine the most predictive next question in response to previous answers. For example, the prediction module 120 may comprise software instructions of a remote server, or software instructions of a local processor, and combinations thereof. Alternatively or in combination, the feature recommendation module 125 may comprise software instructions of a remote server, or software instructions of a local processor, and combinations thereof, configured to determine the most predictive next question, for example. The exemplary operational flow 600 of method of determining an expected feature importance determination algorithm 127 as performed by a feature recommendation module 125 described herein can be performed with one or more processors as described herein, for example.

Figure 7:
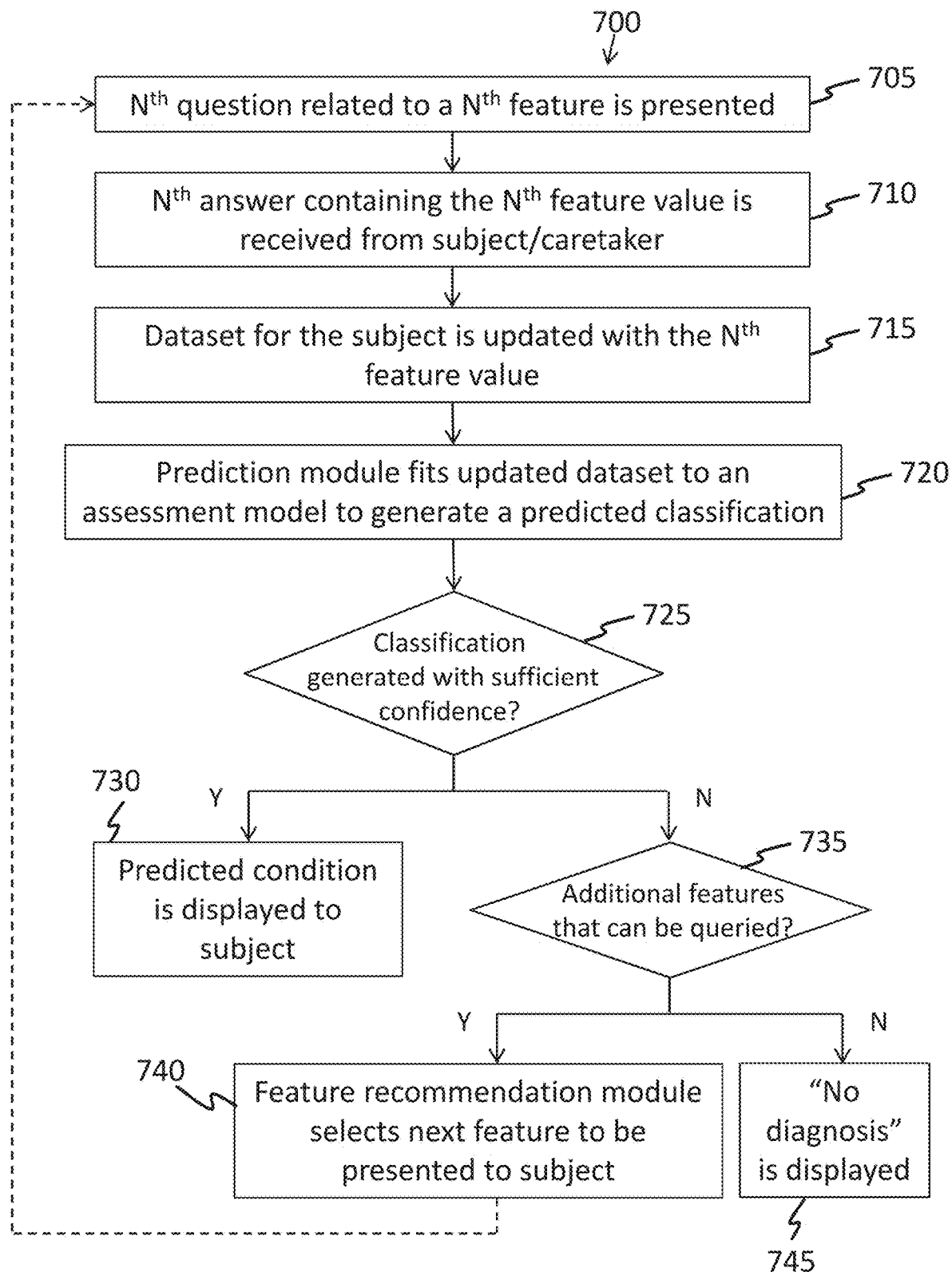
FIG. 7 illustrates a method of administering an assessment procedure as described herein.

FIG. 7 illustrates a method 700 of administering an assessment procedure as described herein. The method 700 may be performed with a user interface provided on a computing device, the computing device comprising a display and a user interface for receiving user input in response to the instructions provided on the display. The user participating in the assessment procedure may be the subject himself, or another person participating in the procedure on behalf of the subject, such as the subject's caretaker. At step 705, an $N^{th}$ question related an $N^{th}$ feature can be presented to the user with the display. At step 710, the subject's answer containing the corresponding $N^{th}$ feature value can be received. At step 715, the dataset for the subject at hand can be updated to include $N^{th}$ the feature value provided for the subject. At step 720, the updated dataset can be fitted to an assessment model to generate a predicted classification. Step 720 may be performed by a prediction module, as described herein. At step 725, a check can be performed to determine whether the fitting of the data can generate a prediction of a specific developmental disorder (e.g., autism, ADHD, etc.) sufficient confidence (e.g., within at least a 90% confidence interval). If so, as shown at step 730, the predicted developmental disorder can be displayed to the user. If not, in step 735, a check can be performed to determine whether there are any additional features that can be queried. If yes, as shown at step 740, the feature recommendation module may select the next feature to be presented to the user, and steps 705-725 may be repeated until a final prediction (e.g., a specific developmental disorder or "no diagnosis") can be displayed to the subject. If no additional features can be presented to the subject, "no diagnosis" may be displayed to the subject, as shown at step 745.

Although the above steps show an exemplary a method 700 of administering an assessment procedure, a person of ordinary skill in the art will recognize many variations based on the teachings described herein. The steps may be completed in a different order. Steps may be added or deleted. Some of the steps may comprise sub-steps of other steps. Many of the steps may be repeated as often as desired by the user.

Figure 8:
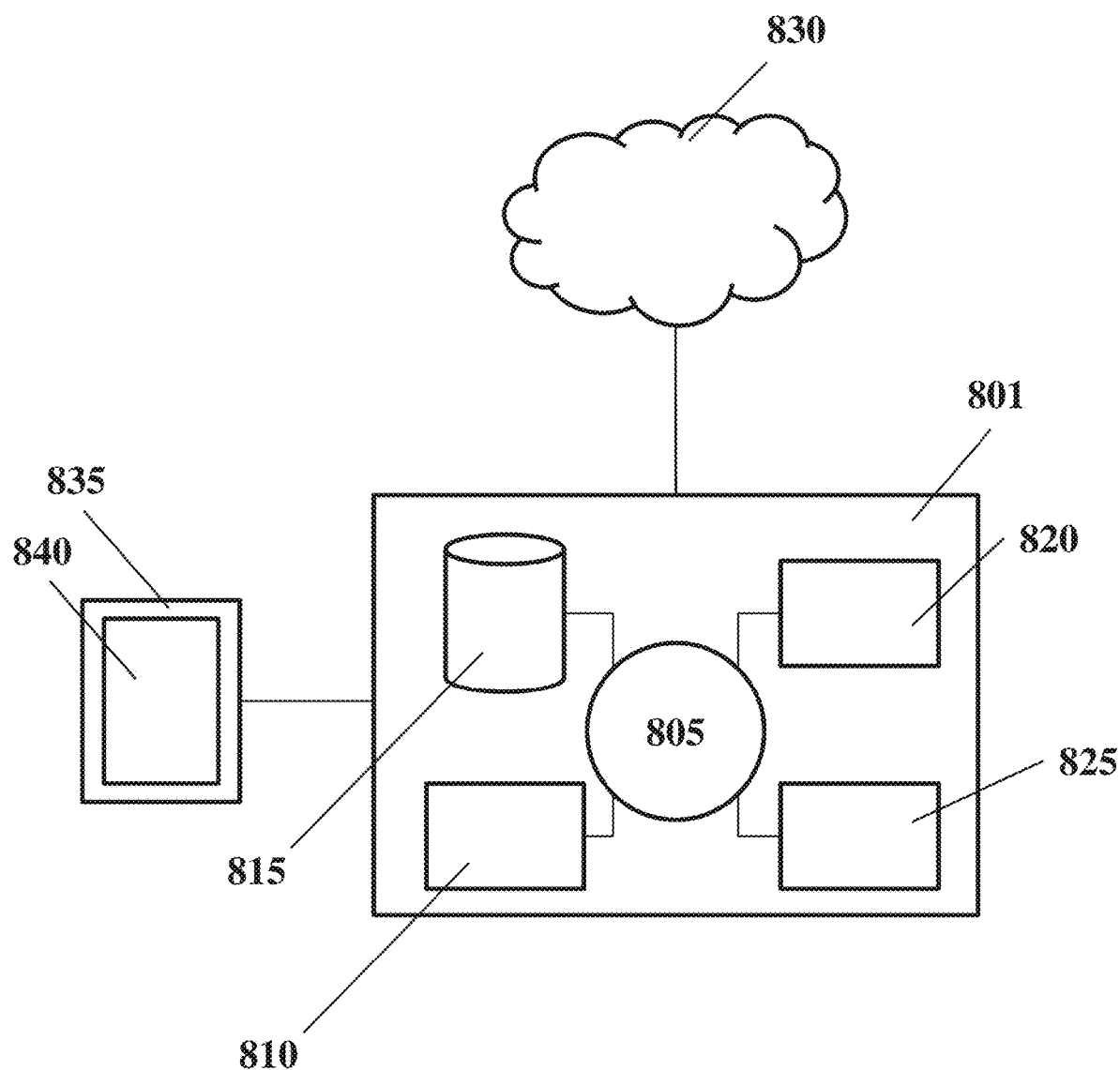
FIG. 8 shows a computer system suitable for incorporation with the methods and apparatus described herein.

The present disclosure provides computer control systems that are programmed to implement methods of the disclosure. FIG. 8 shows a computer system 801 suitable for incorporation with the methods and apparatus described herein. The computer system 801 can process various aspects of information of the present disclosure, such as, for example, questions and answers, responses, statistical analyses. The computer system 801 can be an electronic device of a user or a computer system that is remotely located with respect to the electronic device. The electronic device can be a mobile electronic device.

The computer system 801 includes a central processing unit (CPU, also "processor" and "computer processor" herein) 805, which can be a single core or multi core processor, or a plurality of processors for parallel processing. The computer system 801 also includes memory or memory location 810 (e.g., random-access memory, read-only memory, flash memory), electronic storage unit 815 (e.g., hard disk), communication interface 820 (e.g., network adapter) for communicating with one or more other systems, and peripheral devices 825, such as cache, other memory, data storage and/or electronic display adapters. The memory 810, storage unit 815, interface 820 and peripheral devices 825 are in communication with the CPU 805 through a communication bus (solid lines), such as a motherboard. The storage unit 815 can be a data storage unit (or data repository) for storing data. The computer system 801 can be operatively coupled to a computer network ("network") 830 with the aid of the communication interface 820. The network 830 can be the Internet, an internet and/or extranet, or an intranet and/or extranet that is in communication with the Internet. The network 830 in some cases is a telecommunication and/or data network. The network 830 can include one or more computer servers, which can enable distributed computing, such as cloud computing. The network 830, in some cases with the aid of the computer system 801, can implement a peer-to-peer network, which may enable devices coupled to the computer system 801 to behave as a client or a server.

The CPU 805 can execute a sequence of machine-readable instructions, which can be embodied in a program or software. The instructions may be stored in a memory location, such as the memory 810. The instructions can be directed to the CPU 805, which can subsequently program or otherwise configure the CPU 805 to implement methods of the present disclosure. Examples of operations performed by the CPU 805 can include fetch, decode, execute, and writeback.

The CPU 805 can be part of a circuit, such as an integrated circuit. One or more other components of the system 801 can be included in the circuit. In some cases, the circuit is an application specific integrated circuit (ASIC).

The storage unit 815 can store files, such as drivers, libraries and saved programs. The storage unit 815 can store user data, e.g., user preferences and user programs. The computer system 801 in some cases can include one or more additional data storage units that are external to the computer system 801, such as located on a remote server that is in communication with the computer system 801 through an intranet or the Internet.

The computer system 801 can communicate with one or more remote computer systems through the network 830. For instance, the computer system 801 can communicate with a remote computer system of a user (e.g., a parent).

Examples of remote computer systems and mobile communication devices include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 801 with the network 830.

Methods as described herein can be implemented by way of machine (e.g., computer processor) executable code stored on an electronic storage location of the computer system 801, such as, for example, on the memory 810 or electronic storage unit 815. The machine executable or machine readable code can be provided in the form of software. During use, the code can be executed by the processor 805. In some cases, the code can be retrieved from the storage unit 815 and stored on the memory 810 for ready access by the processor 805. In some situations, the electronic storage unit 815 can be precluded, and machine-executable instructions are stored on memory 810.

The code can be pre-compiled and configured for use with a machine have a processer adapted to execute the code, or can be compiled during runtime. The code can be supplied in a programming language that can be selected to enable the code to execute in a pre-compiled or as-compiled fashion.

Aspects of the systems and methods provided herein, such as the computer system 801, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 801 can include or be in communication with an electronic display 835 that comprises a user interface (UI) 840 for providing, for example, questions and answers, analysis results, recommendations. Examples of UI's include, without limitation, a graphical user interface (GUI) and web-based user interface.

Methods and systems of the present disclosure can be implemented by way of one or more algorithms and with instructions provided with one or more processors as disclosed herein. An algorithm can be implemented by way of software upon execution by the central processing unit 805. The algorithm can be, for example, random forest, graphical models, support vector machine or other.

Although the above steps show a method of a system in accordance with an example, a person of ordinary skill in the art will recognize many variations based on the teaching described herein. The steps may be completed in a different order. Steps may be added or deleted. Some of the steps may comprise sub-steps. Many of the steps may be repeated as often as if beneficial to the platform.

Each of the examples as described herein can be combined with one or more other examples. Further, one or more components of one or more examples can be combined with other examples.

Experimental Data

A data processing module as described herein was built on Python 2.7, Anaconda Distribution. The training data used to construct and train the assessment model included data generated by the Autism Genetic Resource Exchange (AGRE), which performed in-home assessments to collect ADI-R and ADOS data from parents and children in their homes. ADI-R comprises a parent interview presenting a total of 93 questions, and yields a diagnosis of autism or no autism. ADOS comprises a semi-structured interview of a child that yields a diagnosis of autism, ASD, or no diagnosis, wherein a child is administered one of four possible modules based on language level, each module comprising about 30 questions. The data included clinical diagnoses of the children derived from the assessments; if a single child had discrepant ADI-R versus ADOS diagnoses, a licensed clinical psychologist assigned a consensus diagnosis for the dataset for the child in question. The training data included a total of 3,449 data points, with 3,315 cases (autism or ASD) and 134 controls (non-spectrum). The features evaluated in the training data targeted 3 key domains: language, social communication, and repetitive behaviors.

A boosted Random Forest classifier was used to build the assessment model as described herein. Prior to training the assessment model on the training data, the training data was pre-processed to standardize the data, and re-encode categorical features in a one-hot representation as described herein. Since the training data was skewed towards individuals with autism or ASD, sample weighting was applied to attribute up to 50 times higher significance to data from non-spectrum individuals compared to data from autistic/ASD individuals. The assessment model was trained iteratively with boosting, updating the weighting of data points after each iteration to increase the significance attributed to data points that were misclassified, and retraining with the updated significances.

Figure 9:
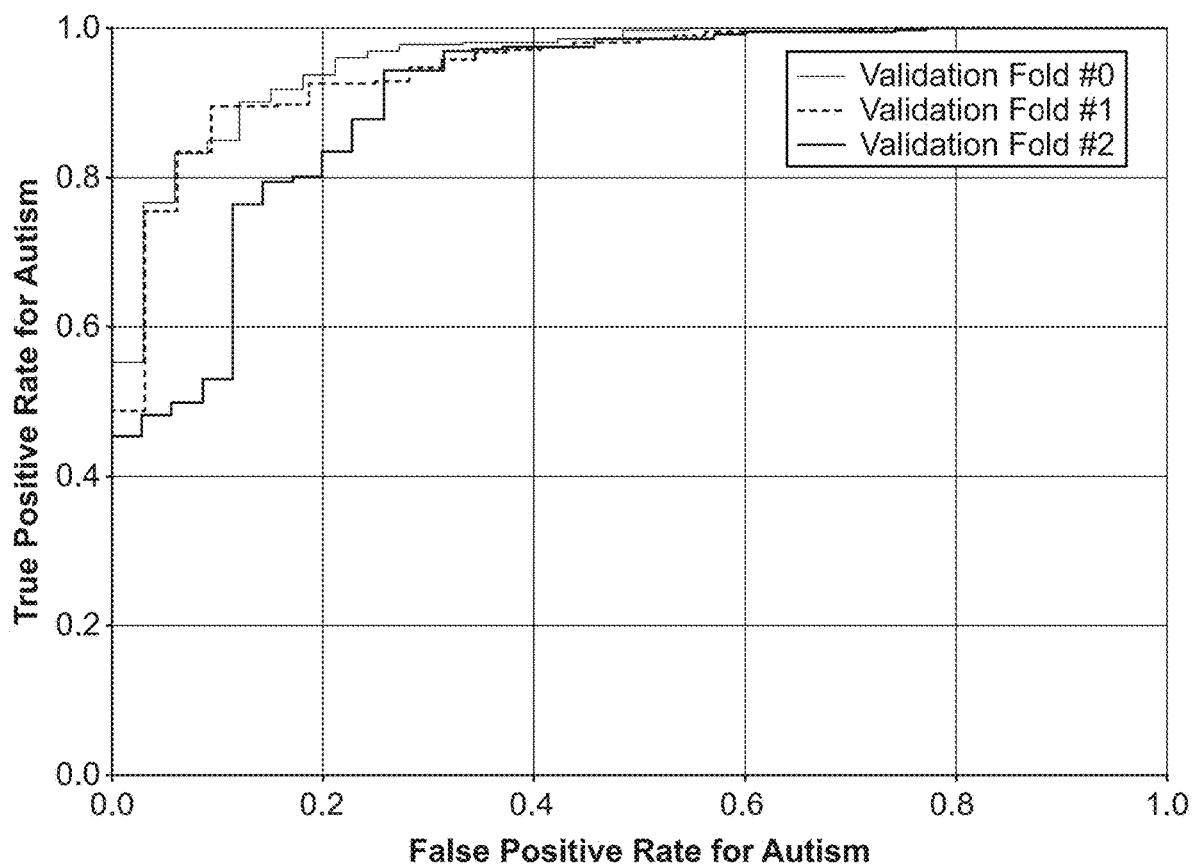
FIG. 9 shows receiver operating characteristic (ROC) curves mapping sensitivity versus fall-out for an exemplary assessment model as described herein.

The trained model was validated using Stratified k-fold cross validation with k=5. The cross-validation yielded an accuracy of about 93-96%, wherein the accuracy is defined as the percentage of subjects correctly classified using the model in a binary classification task (autism/non-spectrum). Since the training data contained a sample bias, a confusion matrix was calculated to determine how often the model confused one class (autism or non-spectrum) with another. The percentage of correctly classified autism individuals was about 95%, while the percentage of correctly classified non-spectrum individuals was about 76%. It should be noted, however, that the model may be adjusted to more closely fit one class versus another, in which case the percentage of correct classifications for each class can change. FIG. 9 shows receiver operating characteristic (ROC) curves mapping sensitivity versus fall-out for an exemplary assessment model as described herein. The true positive rate (sensitivity) for the diagnosis of autism is mapped on the y-axis, as a function of the false positive rate (fall-out) for diagnosis mapped on the x-axis. Each of the three curves, labeled "Fold #0", "Fold #1", and "Fold #2", corresponds to a different "fold" of the cross-validation procedure, wherein for each fold, a portion of the training data was fitted to the assessment model while varying the prediction confidence threshold necessary to classify a dataset as "autistic". As desired or appropriate, the model may be adjusted to increase the sensitivity in exchange for some increase in fall-out, or to decrease the sensitivity in return for a decrease in fall-out, as according to the ROC curves of the model.

Figure 10:
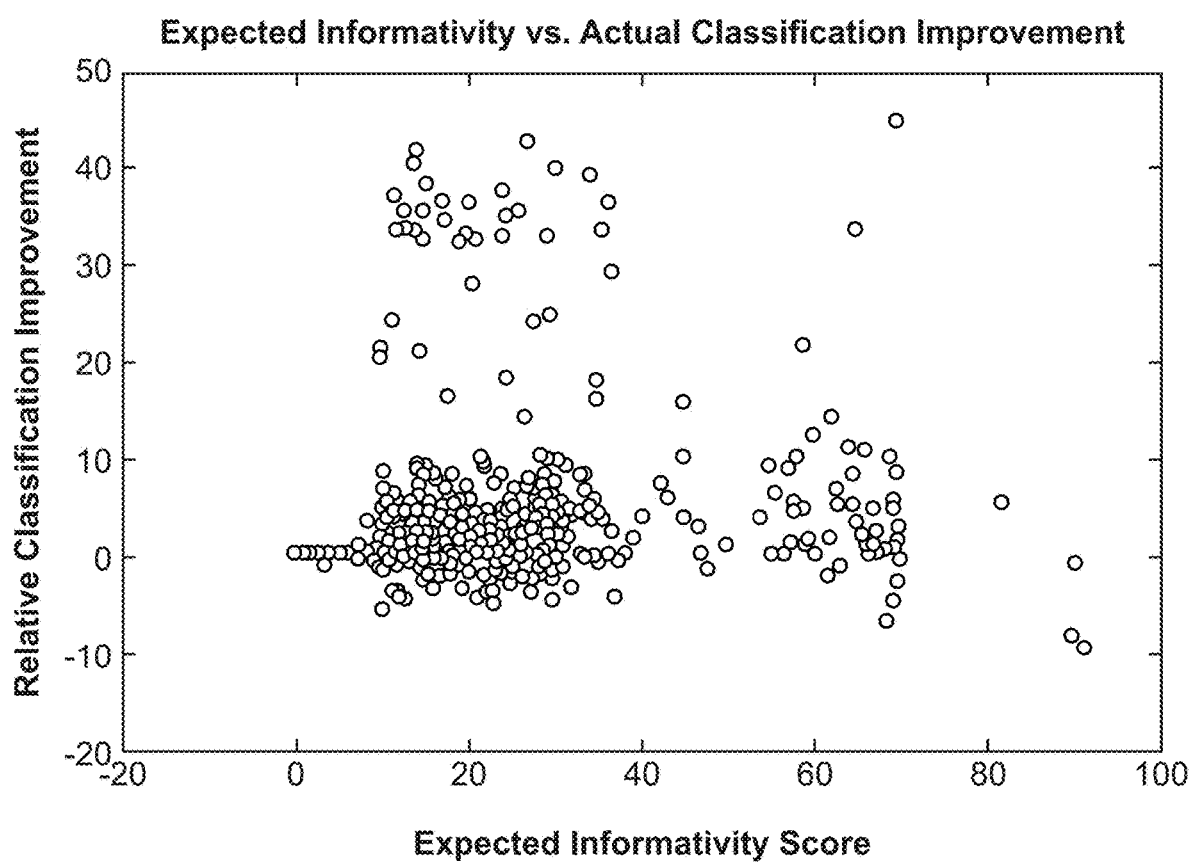
FIG. 10 is a scatter plot illustrating a performance metric for a feature recommendation module as described herein.

The feature recommendation module was configured as described herein, wherein the expected feature importance of each question was computed, and candidate questions ranked in order of computed importance with calls to a server with an application program interface (API). The feature recommendation module's ability to recommend informative questions was evaluated by determining the correlation between a question's recommendation score with the increase in prediction accuracy gained from answering the recommended question. The following steps were performed to compute the correlation metric: (1) the data was split up into folds for cross-validation; (2) already answered questions were randomly removed from the validation set; (3) expected feature importance (question recommendation/score) was generated for each question; (4) one of the questions removed in step 2 was revealed, and the relative improvement in the subsequent prediction accuracy was measured; and (5) the correlation between the relative improvement and the expected feature importance was computed. The calculated Pearson correlation coefficient ranged between 0.2 and 0.3, indicating a moderate degree of correlation between the expected feature importance score and the relative improvement. FIG. 10 is a scatter plot showing the correlation between the expected feature importance ("Expected Informativitiy Score") and the relative improvement ("Relative Classification Improvement") for each question. The plot shows a moderate linear relationship between the two variables, demonstrating the feature recommendation module is indeed able to recommend questions that would increase the prediction accuracy.

The length of time to produce an output using the developed prediction module and the feature recommendation model was measured. The prediction module took about 46 ms to make a prediction of an individual's risk of autism. The feature recommendation module took about 41 ms to generation question recommendations for an individual. Although these measurements were made with calls to a server through an API, the computations can be performed locally, for example.

While the assessment model of the data processing module described with respect to FIGS. 9-10 was constructed and trained to classify subjects as having autism or no autism, a similar approach may be used to build an assessment model that can classify a subject as having one or more of a plurality of developmental disorders, as described herein.

A person of ordinary skill in the art can generate and obtain additional datasets and improve the sensitivity and specificity and confidence interval of the methods and apparatus disclosed herein to obtain improved results without undue experimentation. Although these measurements were performed with example datasets, the methods and apparatus can be configured with additional datasets as described herein and the subject identified as at risk with a confidence interval of 80% in a clinical environment without undue experimentation. The sensitivity and specificity of 80% or more in a clinical environment can be similarly obtained with the teachings provided herein by a person of ordinary skill in the art without undue experimentation, for example with additional datasets.

Additional datasets may be obtained from large archival data repositories as described herein, such as the Autism Genetic Resource Exchange (AGRE), Boston Autism Consortium (AC), Simons Foundation, National Database for Autism Research, and the like. Alternatively or in combination, additional datasets may comprise mathematically simulated data, generated based on archival data using various simulation algorithms. Alternatively or in combination, additional datasets may be obtained via crowd-sourcing, wherein subjects self-administer the assessment procedure as described herein and contribute data from their assessment. In addition to data from the self-administered assessment, subjects may also provide a clinical diagnosis obtained from a qualified clinician, so as to provide a standard of comparison for the assessment procedure.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. An apparatus for treating a subject for autism spectrum disorder, said apparatus comprising:
 a processor; and
 a non-transitory computer readable storage medium including instructions that, when executed by said processor, cause said processor to:

(a) receive a first input corresponding to a first feature from a set of features, wherein said set of features corresponds to one or more clinical characteristics of said subject related to said autism spectrum disorder and a related developmental disorder;

(b) determine, based at least in part on said first input corresponding to said first feature, that said subject has a greater risk of (i) said autism spectrum disorder than (ii) said related developmental disorder;

(c) in response to determining said subject has said greater risk of said autism spectrum disorder than said related developmental disorder, identify a second feature from said set of features, wherein said second feature is most predictive of said autism spectrum disorder, wherein said second feature is identified based at least in part on a first expectation value of said second feature being greater than a second expectation value of a third feature, wherein:

(i) said first expectation value is based at least in part on a plurality of first predictive utilities of each of a plurality of first possible inputs for said second feature and a plurality of first probabilities of occurrence of each of said plurality of first possible inputs for said second feature, wherein each of said plurality of first probabilities of occurrence is determined based at least in part on said first feature and a first constant coefficient that is determined by a trained assessment model, and (ii) said second expectation value is based at least in part on a plurality of second predictive utilities of each of a plurality of second possible inputs for said third feature and a plurality of second probabilities of occurrence of each of said plurality of second possible inputs for said third feature, wherein each of said plurality of second probabilities of occurrence is determined based at least in part on said first feature and a second constant coefficient that is determined by said trained assessment model;

(d) receive a second input corresponding to said second feature that is most predictive of said autism spectrum disorder;

(e) determine, based at least in part on said first input corresponding to said first feature and said second input corresponding to said second feature, that said subject has said greater risk of said autism spectrum disorder than said related developmental disorder; and (f) responsive to said determining in (e), provide a therapy to said subject to treat said autism spectrum disorder, wherein said therapy comprises applied behavioral analysis (ABA) or speech therapy.

2. The apparatus of claim 1, further comprising:
an interface; and
a display coupled to said interface;
  wherein said instructions further cause said processor to display said first feature and receive said first input via said interface.

3. The apparatus of claim 2, wherein said display comprises at least one of a graphical user interface or a web-based user interface.

4. The apparatus of claim 1, wherein said instructions further cause said processor to receive a third input corresponding to said third feature, wherein said third feature is second most predictive of said autism spectrum disorder.

5. The apparatus of claim 1, wherein said instructions further cause said processor to evaluate a dataset comprising said first input to generate a predicted risk of said autism spectrum disorder.

6. The apparatus of claim 1, wherein said instructions further cause said processor to iteratively repeat operations (a) through (d), replacing said first input of said first feature with said second input of said second feature for each iteration, until a predicted risk of said autism spectrum disorder meets a threshold confidence.

7. The apparatus of claim 1, wherein said instructions further cause said processor to identify a first plurality of most predictive next features comprising said second feature.

8. The apparatus of claim 7, wherein said instructions further cause said processor to receive a plurality of inputs corresponding to said first plurality of most predictive next features.

9. The apparatus of claim 8, wherein said instructions further cause said processor to determine a second plurality of most predictive next features based at least in part on said plurality of inputs to said first plurality of most predictive next features.

10. The method of claim 8, further comprising:
determining a second plurality of most predictive next features based at least in part on said plurality of inputs to said first plurality of most predictive next features.

11. The apparatus of claim 1, wherein said plurality of first predictive utilities of each of said plurality of first possible inputs for said second feature corresponds to a correlation of said each of said plurality of first possible inputs with a clinical diagnosis of said autism spectrum disorder.

12. The apparatus of claim 1, wherein said each of said plurality of first probabilities of occurrence is determined based at least in part on applying a nonlinear function to said first feature and said first constant coefficient.

13. The apparatus of claim 12, wherein said trained assessment model comprises a machine learning algorithm comprising one or more of: a binary tree, a random forest, a decision stump, functional tree, logistic model tree, a decision tree, a plurality of decision trees, a plurality of decision trees with controlled variance, a neural network, a support vector machine, a multinomial logistic regression, a naive Bayes classifier, a linear classifier, an ensemble of linear classifiers, a boosting algorithm, a boosting algorithm trained with stochastic gradient descent, a boosting algorithm comprising training data weighting, a boosting algorithm comprising updating training data weighting, or a boosting algorithm comprising updating misclassified training data with higher weights.

14. The apparatus of claim 1, wherein said second feature has a low covariance with said first feature.

15. The apparatus of claim 1, wherein said instructions further cause said processor to determine whether said subject has said greater risk of (i) said autism spectrum disorder of or (ii) said related developmental disorder of said two or more related developmental disorders, with one or both of a confidence interval of at least 85% or a sensitivity and specificity of at least 85%.

16. The apparatus of claim 1, wherein said instructions further cause said processor to determine whether said subject has said greater risk of (i) said autism spectrum disorder or (ii) said related developmental disorder of said two or more related developmental disorders, with one or both of a confidence interval of at least 90% or a sensitivity and specificity of at least 90%.

17. The method of claim 1, wherein said plurality of first predictive utilities of each of said plurality of first possible inputs for said second feature corresponds to a correlation of said each of said plurality of first possible inputs with a clinical diagnosis of said autism spectrum disorder.

18. The apparatus of claim 1, wherein said related developmental disorder comprises one or more of pervasive developmental disorder not otherwise specified (PDD-NOS), attention deficit hyperactivity disorder (ADHD), speech and language delay, obsessive-compulsive disorder (OCD), or social communication disorder.

19. The apparatus of claim 1, wherein said processor comprises one or more of a local processor or a remote server, and wherein said instructions further cause said processor to select said second feature that is most predictive of said autism spectrum disorder with statistics stored on one or more of said local processor or said remote server.

20. The apparatus of claim 1, wherein said therapy comprises said ABA.

21. The apparatus of claim 1, wherein said therapy comprises said speech therapy.

22. A method for treating a subject for autism spectrum disorder, said method comprising:
  (a) receiving a first input corresponding to a first feature from a set of features, wherein said set of features corresponds to one or more clinical characteristics of said subject related to said autism spectrum disorder and a related developmental disorder;
  (b) determining, based at least in part on said first input corresponding to said first feature, that said subject has a greater risk of (i) said autism spectrum disorder than (ii) said related developmental disorder;
  (c) in response to determining said subject has said greater risk of said first developmental disorder than said second developmental disorder, identifying a second feature from said set of features, wherein said second feature is most predictive of said autism spectrum disorder, wherein said second feature is identified based at least in part on a first expectation value of said second feature being greater than a second expectation value of a third feature, wherein:
    (i) said first expectation value is based at least in part on a plurality of first predictive utilities of each of a plurality of first possible inputs for said second feature and a plurality of first probabilities of occurrence of each of said plurality of first possible inputs for said second feature, wherein each of said plurality of first probabilities of occurrence is determined based at least in part on said first feature and a first constant coefficient that is determined by a trained assessment model, and
    (ii) said second expectation value is based at least in part on a plurality of second predictive utilities of each of a plurality of second possible inputs for said third feature and a plurality of second probabilities of occurrence of each of said plurality of second possible inputs for said third feature, wherein each of said plurality of second probabilities of occurrence is determined based at least in part on said first feature and a second constant coefficient that is determined by said trained assessment model;
  (d) receiving a second input corresponding to said second feature that is most predictive of said autism spectrum disorder;
  (e) determining, based at least in part on said first input corresponding to said first feature and said second input corresponding to said second feature, that said subject has said greater risk of said autism spectrum disorder than said related developmental disorder; and
  (f) responsive to said determining in (e), providing a therapy to the subject to treat said autism spectrum disorder, wherein said therapy comprises applied behavioral analysis (ABA) or speech therapy.

23. The method of claim 22, wherein said related developmental disorder comprises one or more of pervasive developmental disorder not otherwise specified (PDD-NOS), attention deficit hyperactivity disorder (ADHD), speech and language delay, obsessive-compulsive disorder (OCD), or social communication disorder.

24. The method of claim 22, further comprising:
  displaying said first feature and receiving said first input via an interface on a display.

25. The method of claim 24, wherein said display comprises at least one of a graphical user interface or a web-based user interface.

26. The method of claim 22, further comprising:
  receiving a third input corresponding to said third feature, wherein said third feature is second most predictive of said autism spectrum disorder.

27. The method of claim 22, further comprising:
  evaluating a dataset comprising said first input to generate a predicted risk of said autism spectrum disorder.

28. The method of claim 22, further comprising:
  iteratively repeating operations (a) through (d), replacing said first input of said first feature with said second input of said second feature for each iteration, until a predicted risk of said autism spectrum disorder meets a threshold confidence.

29. The method of claim 22, further comprising:
  identifying a first plurality of most predictive next features comprising said second feature.

30. The method of claim 29, further comprising:
  receiving a plurality of inputs corresponding to said first plurality of most predictive next features.

31. The method of claim 22, wherein said therapy comprises said ABA.

32. The method of claim 22, wherein said therapy comprises said speech therapy.

33. The method of claim 22, wherein said each of said plurality of first probabilities of occurrence is determined based at least in part on applying a nonlinear function to said first feature and said first constant coefficient.

34. The method of claim 33, wherein said trained assessment model comprises a machine learning algorithm comprising one or more of: a binary tree, a random forest, a decision stump, functional tree, logistic model tree, a decision tree, a plurality of decision trees, a plurality of decision trees with controlled variance, a neural network, a support vector machine, a multinomial logistic regression, a naive Bayes classifier, a linear classifier, an ensemble of linear classifiers, a boosting algorithm, a boosting algorithm trained with stochastic gradient descent, a boosting algorithm comprising training data weighting, a boosting algorithm comprising updating training data weighting, or a boosting algorithm comprising updating misclassified training data with higher weights.

35. The method of claim 22, wherein said second feature has a low covariance with said first feature.

36. The method of claim 22, further comprising:
  determining whether said subject has said greater risk of (i) said autism spectrum disorder or (ii) said related developmental disorder of said two or more related developmental disorders, with one or both of a confidence interval of at least 85% or a sensitivity and specificity of at least 85%.

37. The method of claim 22, further comprising:

determining whether said subject has said greater risk of (i) said autism spectrum disorder or (ii) said related developmental disorder of said two or more related developmental disorders, with one or both of a confidence interval of at least 90% or a sensitivity and specificity of at least 90%.

* * * * *

UNITED STATES PATENT AND TRADEMARK OFFICE
CERTIFICATE OF CORRECTION

| | |
|---|---|
| PATENT NO. | : 12,402,840 B2 |
| APPLICATION NO. | : 16/951915 |
| DATED | : September 2, 2025 |
| INVENTOR(S) | : Brent Vaughan et al. |

Page 1 of 1

It is certified that error appears in the above-identified patent and that said Letters Patent is hereby corrected as shown below:

In the Claims

Claim 15, Line 57:
Replace "disorder of or (ii) said related" with --disorder or (ii) said related--.

Signed and Sealed this
Seventh Day of October, 2025

John A. Squires
*Director of the United States Patent and Trademark Office*